US009751936B2

(12) United States Patent
Papadopoulos

(10) Patent No.: US 9,751,936 B2
(45) Date of Patent: Sep. 5, 2017

(54) HUMAN ANTIBODIES TO SERUM RESISTANCE-ASSOCIATED PROTEIN FROM TRYPANOSOMA BRUCEI RHODESIENSE

(71) Applicant: REGENERON PHARMACEUTICALS, INC., Tarrytown, NY (US)

(72) Inventor: Nicholas J. Papadopoulos, Lagrangeville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 14/768,182

(22) PCT Filed: Feb. 26, 2014

(86) PCT No.: PCT/US2014/018469
§ 371 (c)(1),
(2) Date: Aug. 14, 2015

(87) PCT Pub. No.: WO2014/137674

PCT Pub. Date: Sep. 12, 2014

(65) Prior Publication Data

US 2015/0376269 A1 Dec. 31, 2015

Related U.S. Application Data

(60) Provisional application No. 61/775,078, filed on Mar. 8, 2013.

(51) Int. Cl.

*C07K 16/00* (2006.01)
*C07K 16/20* (2006.01)

(52) U.S. Cl.

CPC .......... *C07K 16/20* (2013.01); *C07K 2317/21* (2013.01); *C07K 2317/34* (2013.01); *C07K 2317/73* (2013.01); *C07K 2317/76* (2013.01); *C07K 2317/92* (2013.01); *C07K 2317/94* (2013.01)

(58) Field of Classification Search

CPC ...................................................... C07K 16/20
See application file for complete search history.

(56) References Cited

U.S. PATENT DOCUMENTS 4,708,930 A * 11/1987 Kortright ............... C07K 16/30
435/104

FOREIGN PATENT DOCUMENTS

WO 2004012757 2/2004

OTHER PUBLICATIONS

Pays Etienne et al., "The Trypanolytic Factor of Human Serum." Nature Reviews, Microbiology; vol. 4, No. 6, pp. 477-486, (Jun. 1, 2006).

Wang Jun et al., "Structural Features Affecting Variant Surface Glycoprotein Expression in Trypanosoma Brucei." Molecular and Biochemical Parasitology vol. 128, No. 2, pp. 135-145, (May 2003).

Clarke M.W. et al., " Structural Features of Antigenic Determinants on Variant Surface Glycoproteins from Trypanosoma Brucei." Molecular Immunology, vol. 24, No. 7, pp. 707-713, (Jul. 1, 1987).

Hall T. et al., "Topologic Mapping of Protective and Nonprotective Epitopes on the Variant Surface Glyco Protein of the Walter Reed Army Trypanozoon Antigen Type 1 Clone of Trypanosoma-Brucei-Rhodesiense." Journal of Immunology, vol. 132, No. 4, pp. 2059-2063, (1984).

Milner J. D. et al., "Expressoin and Localization of Serum Resistance associated protein in Trypanosoma Brucei Rhodesiense" Molecular and Biochemical Parasitology, vol. 104, No. 2, pp. 271-283, (Nov. 30, 1999).

Vanhamme L. et al., "Apolipoprotein L-I is the Trypanosome Lytic Factor of Human Serum." Nature, vol. 422, No. 6927, pp. 83-87, (Mar. 6, 2003).

* cited by examiner

*Primary Examiner* — Albert Navarro

(74) *Attorney, Agent, or Firm* — Aparna Patankar; Frank Cottingham; Karl Bozicevic

(57) ABSTRACT

The present invention provides antibodies that bind to serum resistance-associated (SRA) protein of *Trypanosoma brucei rhodesiense*, and methods of use. According to certain embodiments of the invention, the antibodies are fully human antibodies that bind to SRA. The antibodies of the invention are useful for inhibiting or neutralizing SRA activity, thus providing a means of treating human African trypanosomiasis (sleeping sickness), and symptoms associated with the disease. The antibodies of the invention may also be useful for diagnosis of sleeping sickness.

22 Claims, 3 Drawing Sheets

Figure 3

HUMAN ANTIBODIES TO SERUM RESISTANCE-ASSOCIATED PROTEIN FROM TRYPANOSOMA BRUCEI RHODESIENSE

FIELD OF THE INVENTION

The present invention is related to human antibodies and antigen-binding fragments of human antibodies that specifically bind to serum resistance-associated protein (SRA) in *Trypanosoma brucei rhodesiense*, and therapeutic and diagnostic methods of using those antibodies.

STATEMENT OF RELATED ART

*Trypanosoma brucei rhodesiense* is the causative agent of the acute form of human African trypanosomiasis, a lethal disease endemic to sub-Saharan Africa. The disease, also known as sleeping sickness, occurs in two forms: one form caused by *T. brucei gambiense* which occurs to the west of the Great Rift Valley; and an acute form caused by *T. brucei rhodesiense* which occurs to the east of the Great Rift Valley in Africa. Trypanosomiasis is a zoonosis transmitted by the tsetse fly (*Glossina* spp.) to humans and animals such as cattle, and wild game. The parasites exhibit several life stages in the mammalian host and in the tsetse fly vector.

*T. brucei rhodesiense* produces a serum resistance-associated (SRA) protein which binds to human apolipoprotein-L1 (apoL1) and neutralizes the trypanolytic activity of human serum. Polyclonal antibodies to SRA have been described by Milner et al 1999 in Mol. Biochem. Parasitol. 104: 271-283 and in U.S. Pat. No. 7,585,511. WO2007039645 describes a nanobody-conjugated trypanolytic factor for treating trypanosomiasis.

BRIEF SUMMARY OF THE INVENTION

The invention provides fully human monoclonal antibodies (mAbs) and antigen-binding fragments thereof that bind specifically to trypanosomal SRA. Such antibodies may be useful to neutralize the activity of SRA and may act to lessen the severity of a sleeping sickness-associated condition or disease, or reduce the number, the duration, or the severity of disease recurrence, or ameliorate at least one symptom associated with the sleeping sickness-associated condition or disease. Such antibodies may be used alone or in conjunction with a second agent useful for treating a sleeping sickness-associated condition or disease. In certain embodiments, the antibodies may be used prophylactically as stand-alone therapy to protect patients who are at risk for developing a sleeping sickness-associated condition or disease.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. Immunol. 164:1925-1933).

Accordingly, in a first aspect, the invention provides an isolated antibody or antigen-binding fragment thereof that specifically binds to trypanosomal SRA. In one embodiment, the invention provides a fully human monoclonal antibody or antigen-binding fragment thereof that specifically binds to SRA.

In certain embodiments, the antibody binds to full-length SRA or a fragment thereof as exemplified by SEQ ID NOS: 289, and 290. In some embodiments, the antibody binds to recombinant SRA or a fragment thereof as exemplified by SEQ ID NOs: 291, 292, 293, 294, 295 or 296. In certain embodiments, the isolated human antibody or antigen-binding fragment thereof binds to SRA with a $K_D$ equal to or less than $10^{-10}$ M, as measured by surface plasmon resonance. In one embodiment, the isolated antibody or antigen-binding fragment thereof binds specifically to SRA at 25° C. and acidic pH with a dissociative half-life (t½) of less than about 4 minutes, wherein the antibody binds to SRA at 25° C. at neutral pH with a t½ of greater than about 20 minutes, as determined by surface plasmon resonance. In one embodiment, the isolated antibody or antigen-binding fragment thereof binds specifically to SRA at 25° C. and acidic pH with a dissociative half-life (t½) of less than about 100 minutes, wherein the antibody binds to SRA at 25° C. at neutral pH with a t½ of greater than about 150 minutes, as determined by surface plasmon resonance. In one embodiment, the isolated antibody or antigen-binding fragment thereof binds specifically to SRA at acidic pH and at neutral pH, wherein the dissociation rate constant (kd) for the antibody binding to SRA at 25° C. is less than about $1.7 \times 10^{-2}$, as determined by surface plasmon resonance.

In one embodiment, the isolated antibody or antigen-binding fragment thereof that binds to SRA blocks SRA binding to human apolipoprotein (apoL1). In one embodiment, the isolated antibody or antigen-binding fragment thereof that binds SRA does not block SRA binding to apoL1.

In one embodiment, the isolated antibody or antigen-binding fragment thereof binds SRA at a pH ranging from about 7.4 to about 4.5. In one embodiment, the isolated antibody or antigen-binding fragment thereof binds to SRA at about pH 7.4 and remains bound at about pH 4.5. In one embodiment, the isolated antibody or antigen-binding fragment thereof that binds to SRA blocks SRA binding to apoL1 at a pH ranging from about 7.4 to about 4.5.

In one embodiment, the isolated antibody or antigen-binding fragment thereof binds specifically to SRA, wherein the antibody or antigen-binding fragment thereof binds to an epitope on SRA (SEQ ID NO: 290) comprising an amino acid selected from the group consisting of S-174, I-175, V-176, K-177, K-178, P-179, K-180, G-181, A-182, P-183, D-184, K-185, T-186, A-187, A-188, D-189, E-190, L-191, V-192, T-193 and A-194.

In one embodiment, the isolated human antibody or antigen-binding fragment thereof which binds to SRA comprises the three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, and 274; and the three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, and 282. Methods and techniques for identifying CDRs within HCVR and LCVR amino acid sequences are well known in the art and can be used to identify CDRs within the specified heavy chain variable region(s) (HCVR) and/or light chain variable region(s) (LCVR) amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches.

See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In one embodiment, the isolated human antibody or antigen-binding fragment thereof which binds to SRA comprises a HCVR having an amino acid sequence selected from the group consisting of SEQ ID NOs: 2, 18, 34, 50, 66, 82, 98, 114, 130, 146, 162, 178, 194, 210, 226, 242, 258, and 274.

In one embodiment, the isolated human antibody or antigen-binding fragment thereof which binds to SRA comprises a LCVR having an amino acid sequence selected from the group consisting of SEQ ID NOs: 10, 26, 42, 58, 74, 90, 106, 122, 138, 154, 170, 186, 202, 218, 234, 250, 266, and 282.

In one embodiment, the isolated human antibody or antigen-binding fragment thereof which binds to SRA comprises (a) a HCVR having an amino acid sequence selected from the group consisting of SEQ ID NOs: 2, 18, 34, 50, 66, 82, 98, 114, 130, 146, 162, 178, 194, 210, 226, 242, 258, and 274; and (b) a LCVR having an amino acid sequence selected from the group consisting of SEQ ID NO: 10, 26, 42, 58, 74, 90, 106, 122, 138, 154, 170, 186, 202, 218, 234, 250, 266, and 282.

In one embodiment, the isolated human antibody or antigen-binding fragment thereof which binds to SRA comprises:
(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, and 276;
(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, and 278;
(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, and 280;
(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, and 284;
(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, and 286; and
(f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, and 288.

In one embodiment, the isolated human antibody or antigen-binding fragment thereof which binds to SRA comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

In one embodiment, the invention provides a fully human monoclonal antibody or antigen-binding fragment thereof that binds to SRA, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 286, or a substantially similar sequence thereof having at least 90%, at least 95%, at least 98% or at least 99% sequence identity; and (v) binds to SRA with a $K_D$ equal to or less than $10^{-10}$, as measured by surface plasmon resonance.

In a second aspect, the invention provides an isolated human monoclonal antibody or antigen-binding fragment thereof that blocks SRA binding to apoL1, wherein the antibody comprises the three heavy chain CDRs (HCDR1, HCDR2 and HCDR3) contained within any one of the HCVR amino acid sequences selected from the group consisting of SEQ ID NOs: 66, 98, 130, 146, 162, 210, 226, 242, 258, and 274; and the three light chain CDRs (LCDR1, LCDR2 and LCDR3) contained within any one of the LCVR amino acid sequences selected from the group consisting of SEQ ID NOs: 74, 106, 138, 154, 170, 218, 234, 250, 266, and 282.

In one embodiment, the isolated human antibody or antigen-binding fragment thereof that blocks SRA binding to apoL1 comprises a HCVR having an amino acid sequence selected from the group consisting of SEQ ID NOs: 66, 98, 130, 146, 162, 210, 226, 242, 258, and 274.

In one embodiment, the isolated human antibody or antigen-binding fragment thereof that blocks SRA binding to apoL1 comprises a LCVR having an amino acid sequence selected from the group consisting of SEQ ID NOs: 74, 106, 138, 154, 170, 218, 234, 250, 266, and 282.

In one embodiment, the isolated human antibody or antigen-binding fragment thereof that blocks SRA binding to apoL1 comprises (a) a HCVR having an amino acid sequence selected from the group consisting of SEQ ID NOs: 66, 98, 130, 146, 162, 210, 226, 242, 258, and 274; and (b) a LCVR having an amino acid sequence selected from the group consisting of SEQ ID NO: 74, 106, 138, 154, 170, 218, 234, 250, 266, and 282.

In one embodiment, the isolated human antibody or antigen-binding fragment thereof that blocks SRA binding to apoL1 comprises:
(a) a HCDR1 domain having an amino acid sequence selected from the group consisting of SEQ ID NOs: 68, 100, 132, 148, 164, 212, 228, 244, 260, and 276;
(b) a HCDR2 domain having an amino acid sequence selected from the group consisting of SEQ ID NOs: 70, 102, 134, 150, 166, 214, 230, 246, 262, and 278;
(c) a HCDR3 domain having an amino acid sequence selected from the group consisting of SEQ ID NOs: 72, 104, 136, 152, 168, 216, 232, 248, 264, and 280;
(d) a LCDR1 domain having an amino acid sequence selected from the group consisting of SEQ ID NOs: 76, 108, 140, 156, 172, 220, 236, 252, 268, and 284;
(e) a LCDR2 domain having an amino acid sequence selected from the group consisting of SEQ ID NOs: 78, 110, 142, 158, 174, 222, 238, 254, 270, and 286; and
(f) a LCDR3 domain having an amino acid sequence selected from the group consisting of SEQ ID NOs: 80, 112, 144, 160, 176, 224, 240, 256, 272, and 288.

In one embodiment, the isolated human antibody or antigen-binding fragment thereof that blocks SRA binding to apoL1 comprises a HCVR/LCVR amino acid sequence pair selected from the group consisting of SEQ ID NOs: 66/74, 98/106, 130/138, 146/154, 162/170, 210/218, 226/234, 242/250, 258/266, and 274/282.

In one embodiment, the invention provides a fully human monoclonal antibody or antigen-binding fragment thereof that blocks SRA binding to apoL1, wherein the antibody or fragment thereof exhibits one or more of the following characteristics: (i) comprises a HCVR having an amino acid sequence selected from the group consisting of SEQ ID NO: 66, 98, 130, 146, 162, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 74, 106, 138, 154, 170, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 72, 104, 136, 152, 168, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 80, 112, 144, 160, 176, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 68, 100, 132, 148, 164, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 70, 102, 134, 150, 166, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 76, 108, 140, 156, 172, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 78, 110, 142, 158, 174, 222, 238, 254, 270, and 286, or a substantially similar sequence thereof having at least 90%, at least 95%, at least 98% or at least 99% sequence identity; (v) binds to SRA with a $K_D$ equal to or less than $10^{-10}$ as determined by surface plasmon resonance; and (vi) blocks binding of SRA to apoL1 at a pH ranging from about 7.4 to about 4.5.

In a related aspect, the invention provides for an isolated antibody or antigen-binding fragment thereof that neutralizes or blocks the human serum resistance activity of SRA comprising the CDRs of a HCVR, wherein the HCVR has an amino acid sequence selected from the group consisting of SEQ ID NOs: 66, 98, 130, 146, 162, 210, 226, 242, 258, and 274; and the CDRs of a LCVR, wherein the LCVR has an amino acid sequence selected from the group consisting of SEQ ID NOs: 74, 106, 138, 154, 170, 218, 234, 250, 266, and 282.

In certain embodiments, the isolated antibody or antigen-binding fragment thereof that blocks SRA binding to apoL1 may bind to the same epitope on SRA as apoL1 or may bind to a different epitope on SRA as apoL1.

In some embodiments, the isolated antibody or antigen-binding fragment thereof that blocks SRA binding to apoL1 binds to one or more amino acids selected from the group consisting of amino acid residues 174-194 of SRA (SEQ ID NO: 290). In one embodiment, the isolated antibody or antigen-binding fragment thereof that blocks SRA binding to apoL1 binds to one or more amino acids of SEQ ID NO: 301.

In a related embodiment, the isolated antibody or antigen-binding fragment thereof that blocks SRA binding to apoL1 binds to an apoL1-binding domain of SRA. In one embodiment, the apoL1-binding domain of SRA comprises amino acids 202-222 of full length SRA.

In one embodiment, the isolated antibody or antigen-binding fragment thereof that blocks SRA binding to apoL1 binds outside the apoL1-binding domain of SRA. In one embodiment, the isolated antibody or antigen-binding fragment thereof may block SRA binding to apoL1 due to steric hindrance.

In a third aspect, the invention provides an isolated antibody or antigen-binding fragment thereof that exhibits binding to SRA over a broad range of pH. In certain embodiments, the invention provides an antibody or antigen-binding fragment thereof that binds to SRA at neutral pH and at acidic pH. In some embodiments, the invention includes an antibody or antigen-binding fragment thereof that binds to SRA at neutral pH and remains bound at acidic pH. For example, the invention includes antibodies or antigen-binding fragments thereof that bind to SRA at pH ranging from about 7.4 to about 4.5. In one embodiment, the isolated antibody or antigen-binding fragment thereof binds to SRA at pH 7.4 and at pH 4.5. In one embodiment, the isolated antibody or antigen-binding fragment thereof binds to SRA at pH 7.4 and remains bound through pH 4.5. For example, the antibody maintains binding to SRA at pH 7.4, 7.0, 6.5, 6.0, 5.5, 5.0 and 4.5.

The binding characteristics of an anti-SRA antibody can be quantified in vitro, e.g., by surface plasmon resonance, which provides numerical values of the binding properties (e.g., ka, $k_d$, $K_D$, t½, etc.) for the antibody binding to SRA at neutral pH and at acidic pH. Binding can be studied at 25° C.

In some embodiments, the invention includes antibodies or antigen-binding fragments thereof that bind to SRA at acidic pH with a t½ of less than about 4 minutes, wherein the antibody binds to SRA at neutral pH with a t½ of greater than about 20 minutes. In one embodiment, the invention includes an antibody or antigen-binding fragment thereof that binds to SRA at acidic pH with a t½ of less than about 100 minutes, wherein the antibody binds to SRA at neutral pH with a t½ of greater than about 150 minutes.

In one embodiment, the invention includes an antibody or antigen-binding fragment thereof that binds to SRA at neutral pH and acidic pH, wherein the kd for the antibody binding to SRA is less than about $1.7 \times 10^{-2}$, as determined by surface plasmon resonance.

In one embodiment, the isolated human antibody or antigen-binding fragment thereof which binds to SRA at a neutral pH and at an acidic pH comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

In one embodiment, the invention provides a fully human monoclonal antibody or antigen-binding fragment thereof that binds to SRA, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 286, or a substantially similar sequence thereof having at least 90%, at least 95%, at least 98% or at least 99% sequence identity; and (v) binds to SRA with a $K_D$ equal to or less than $10^{-10}$ as determined by surface plasmon resonance; and (vi) binds to SRA at a pH ranging from about 7.4 to about 4.5.

In related embodiments, the antibodies or antigen-binding fragments that bind to SRA at acidic pH block or prevent SRA binding to apoL1.

In certain embodiments, the isolated human antibody or antigen-binding fragment thereof that binds to SRA at acidic pH and blocks SRA binding to apoL1 comprises a HCVR/LCVR amino acid sequence pair selected from the group consisting of SEQ ID NOs: 66/74, 98/106, 130/138, 146/154, 162/170, 210/218, 226/234, 242/250, 258/266, and 274/282.

In one embodiment, the invention provides a fully human monoclonal antibody or antigen-binding fragment thereof that binds to SRA at acidic pH and blocks SRA binding to apoL1, wherein the antibody or fragment thereof exhibits one or more of the following characteristics: (i) comprises a HCVR having an amino acid sequence selected from the group consisting of SEQ ID NO: 66, 98, 130, 146, 162, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 74, 106, 138, 154, 170, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 72, 104, 136, 152, 168, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 80, 112, 144, 160, 176, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 68, 100, 132, 148, 164, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 70, 102, 134, 150, 166, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 76, 108, 140, 156, 172, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 78, 110, 142, 158, 174, 222, 238, 254, 270, and 286, or a substantially similar sequence thereof having at least 90%, at least 95%, at least 98% or at least 99% sequence identity; (v) binds to SRA with a $K_D$ equal to or less than $10^{-10}$; (vi) binds to SRA at a pH ranging from about 7.4 to about 4.5; and (vii) blocks binding of SRA to apoL1 at pH 4.5.

In a fourth aspect, the invention provides an isolated antibody or antigen-binding fragment thereof that competes for specific binding to SRA with an antibody or antigen-binding fragment comprising the CDRs of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, and 274; and the CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, and 282.

In one embodiment, the invention provides an isolated antibody or antigen-binding fragment thereof that competes for specific binding to SRA with an antibody or antigen-binding fragment comprising the heavy and light chain CDRs contained within heavy and light chain sequence pairs selected from the group consisting of SEQ ID NOs: 66/74, 98/106, 130/138, 146/154, 162/170, 210/218, 226/234, 242/250, 258/266, and 274/282.

In one embodiment, the invention provides an isolated antibody or antigen-binding fragment thereof that binds the same epitope on SRA as an antibody or antigen-binding fragment comprising the CDRs of a HCVR, wherein the HCVR has an amino acid sequence selected from the group consisting of SEQ ID NOs: 66, 98, 130, 146, 162, 210, 226, 242, 258, and 274; and the CDRs of a LCVR, wherein the LCVR has an amino acid sequence selected from the group consisting of SEQ ID NOs: 74, 106, 138, 154, 170, 218, 234, 250, 266, and 282.

In a related embodiment, the invention provides an isolated antibody or antigen-binding fragment thereof that binds the same epitope on SRA as an antibody or antigen-binding fragment comprising the heavy and light chain CDRs contained within heavy and light chain sequence pairs selected from the group consisting of SEQ ID NOs: 66/74, 98/106, 130/138, 146/154, 162/170, 210/218, 226/234, 242/250, 258/266, and 274/282.

In certain embodiments, the isolated antibody or antigen-binding fragment thereof binds to an epitope on SRA comprising an amino acid selected from the group consisting of amino acid residues 202-222 of full length SRA (SEQ ID NO: 289). In one embodiment, the isolated antibody or antigen-binding fragment thereof binds to an epitope on SRA comprising an amino acid selected from the group consisting of amino acid residues 202-220 of full length SRA (SEQ ID NO: 289). In one embodiment, the isolated antibody or antigen-binding fragment thereof binds to an epitope on SRA comprising an amino acid selected from the group consisting of amino acid residues 174-194 of SEQ ID NO: 290.

In a related embodiment, the invention provides an isolated antibody or antigen-binding fragment thereof that binds to the apoL1-binding domain of SRA. In another embodiment, the invention provides an isolated antibody or antigen-binding fragment thereof that binds outside the apoL1-binding domain of SRA.

In a fifth aspect, the invention provides nucleic acid molecules encoding anti-SRA antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, and 273, or a substantially identical sequence having at least 90%, at least 95%, at least 98%, or at least 99% homology thereof.

In one embodiment, the antibody or fragment thereof comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, and 281, or a substantially identical sequence having at least 90%, at least 95%, at least 98%, or at least 99% homology thereof.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, and 279, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, and 287, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, and 275, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, and 277, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, and 283, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, and 285, or a substantially similar sequence thereof having at least 90%, at least 95%, at least 98% or at least 99% sequence identity.

In a sixth aspect, the invention provides a pharmaceutical composition comprising an isolated antibody or antigen-binding fragment thereof that binds specifically to SRA and a pharmaceutically acceptable carrier or diluent. In one embodiment, the invention provides a pharmaceutical composition comprising an isolated fully human monoclonal antibody or antigen-binding fragment thereof that binds to an epitope comprising an amino acid selected from the group consisting of amino acid residues 174-194 of SRA (SEQ ID NO: 290) and a pharmaceutically acceptable carrier or diluent. In one embodiment, the invention provides a pharmaceutical composition comprising an isolated fully human monoclonal antibody or antigen-binding fragment thereof that binds specifically to an N-terminal fragment of SRA and a pharmaceutically acceptable carrier or diluent.

In one embodiment, the invention provides a pharmaceutical composition comprising two fully human monoclonal antibodies or antigen-binding fragments thereof that bind to SRA, one that blocks SRA binding to apoL1 and one that does not block SRA binding to apoL1 and a pharmaceutically acceptable carrier or diluent. In one embodiment, the invention provides a pharmaceutical composition comprising one dual binding fully human monoclonal antibody (an antibody that binds to both the apoL1-binding domain and outside the apoL1-binding domain of SRA) and a pharmaceutically acceptable carrier or diluent. In one embodiment, the invention provides a pharmaceutical composition comprising two or more dual binding fully human monoclonal antibodies and a pharmaceutically acceptable carrier or diluent. It is to be understood that any combination of antibodies as described herein may be used in a pharmaceutical composition to achieve the desired results in the patient population in need of such therapy. For example, two antibodies that recognize and/or bind only apoL1-binding domain of SRA may be used in a composition. Alternatively, two antibodies that recognize and/or bind outside the apoL1-binding domain of SRA may be used in a composition. In one embodiment, one antibody that recognizes/binds to only the apoL1-binding domain or a non-apoL1-binding domain of SRA may be combined with a dual binding antibody in a composition.

Embodiments of the invention encompass pharmaceutical compositions comprising bispecific or multispecific antibodies (as disclosed elsewhere herein) or combinations of individual, dual or multispecific antibodies to SRA.

In one embodiment, the composition comprises an antibody that binds to SRA and has a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

In one embodiment, the pharmaceutical composition comprises an isolated first fully human monoclonal antibody or antigen-binding fragment thereof that specifically binds to the apoL1-binding domain of SRA, as described herein, and an isolated second fully human monoclonal antibody or antigen-binding fragment thereof that specifically binds outside the apoL1-binding domain of SRA, as described herein, and a pharmaceutically acceptable carrier or diluent.

In one embodiment, the invention features a composition, which is a combination of an antibody or antigen-binding fragment of an antibody of the invention, and a second therapeutic agent.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with the antibody or fragment thereof of the invention, for example, an antibiotic, an anti-inflammatory drug, a non-steroidal anti-inflammatory drug (NSAID), a nutritional supplement, or a second different antibody against SRA or any other antigen from *T. brucei rhodesiense*, or an anti-trypanosomal agent such as suramin, melarsoprol, eflornithine or nifurtimox.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents which are normally administered to treat or prevent a particular disease, or condition, are appropriate for the disease, or condition, being treated. When multiple therapeutics are co-administered, dosages may be adjusted accordingly, as is recognized in the pertinent art.

A seventh aspect of the invention provides for methods of treating a patient suffering from sleeping sickness, or for treating at least one symptom or complication associated with sleeping sickness, or for treating a patient at risk for developing sleeping sickness, the method comprising administering to the patient an effective amount of an antibody or an antigen-binding fragment thereof that binds to SRA; or a pharmaceutical composition comprising a therapeutically effective amount of an antibody or an antigen-binding fragment thereof that binds to SRA, such that the sleeping sickness-associated condition or disease is either prevented, or lessened in severity and/or duration, or at least one symptom or complication associated with the condition or disease is prevented, or ameliorated, or that the frequency and/or duration of, or the severity of sleeping sickness is reduced. In one embodiment, the antibody is administered therapeutically (administered after sleeping sickness has been established and given throughout the course of the condition) to a patient suffering from sleeping sickness-associated condition or disease, or suffering from at least one symptom or complication associated with the condition or disease. In one embodiment, the antibody is administered prophylactically (administered prior to development of the condition) to a patient at risk for developing sleeping sickness-associated condition or disease. For example, such "patients at risk for developing sleeping sickness" include people in regions of heavy infestation with tsetse flies, hunters and other visitors to Africa including visitors to safari parks, children born to infected mothers, and people who have had sexual contact with or blood transfusion from infected persons.

In one embodiment, the pharmaceutical composition comprising the antibodies of the invention is administered to the patient in combination with a second therapeutic agent.

In another embodiment, the second therapeutic agent is selected from the group consisting of an anti-inflammatory drug, a NSAID, a nutritional supplement such as an antioxidant, another antibody to SRA or any other trypanosomal antigen, an anti-trypanosomal agent such as suramin, melarsoprol, eflornithine or nifurtimox, apoL1 variant, and any other therapy useful for ameliorating at least one symptom associated with a sleeping sickness-associated condition or disease.

In some embodiments, the at least one symptom or complication associated with the sleeping sickness-associated condition or disease is selected from the group consisting of fever, headaches, joint pain, itching, severe swelling of the lymph nodes, anemia, endocrine, cardiac or kidney dysfunction, confusion, reduced co-ordination, disruption of the sleep cycle with bouts of fatigue punctuated by manic periods leading to daytime slumber and night-time insomnia, rapid degradation in the quality of life, and death of the patient suffering from the sleeping sickness-condition or disease.

In embodiments of the invention, the antibody or antigen-binding fragment thereof or the pharmaceutical composition comprising the antibody is administered subcutaneously, intravenously, intradermally, orally, intraperitoneally, intramuscularly or intracranially. In some embodiments, the antibody or antigen-binding fragment thereof is administered at doses of about 0.1 mg/kg of body weight to about 60 mg/kg of body weight, more specifically about 5 mg/kg of body weight to about 50 mg/kg of body weight.

In related embodiments, the invention includes the use of an isolated anti-SRA antibody or antigen binding portion of an antibody of the invention in the manufacture of a medicament for the treatment of a disease or disorder related to or caused by SRA activity. In one embodiment, the invention includes the use of an anti-SRA antibody of the invention in the manufacture of a medicament for treating a patient suffering from or at risk of developing sleeping sickness.

An eighth aspect of the invention provides for methods of diagnosing sleeping sickness in a patient, the method comprising reacting a SRA protein from the patient with an antibody or antigen-binding fragment of the invention, wherein binding with SRA indicates presence of sleeping sickness.

In one embodiment, the invention features a method of predicting poor survival in a patient suffering from sleeping sickness, the method comprising reacting a SRA protein from the patient with an isolated antibody of the invention as described herein, wherein strong binding with SRA indicates poor survival.

In one embodiment, the SRA from a patient is obtained from the patient's blood, serum, plasma, or biopsy of a tissue.

Other embodiments will become apparent from a review of the ensuing detailed description.

BRIEF DESCRIPTION OF THE FIGURES

FIG. 3 shows the results of the 31×31 octet cross competition assay.

DETAILED DESCRIPTION

Figure 1:
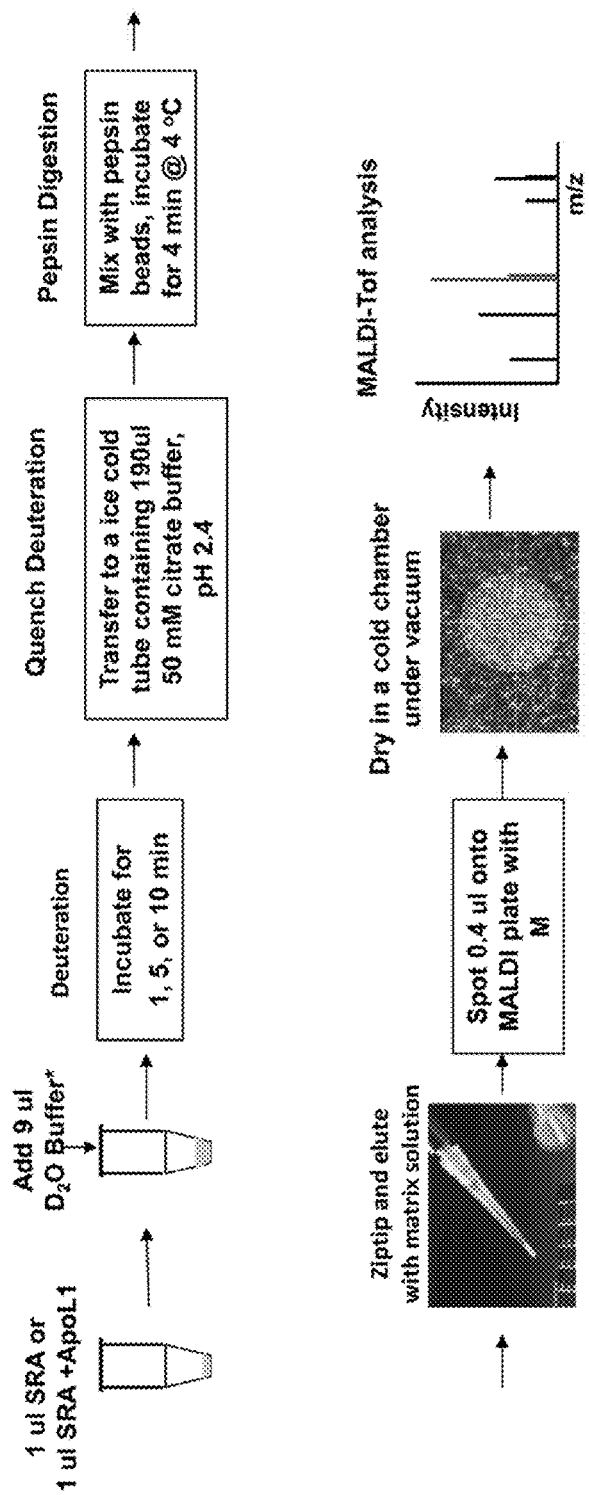
FIG. 1 is a schematic representation of the protocol used for H/DX epitope mapping of SRA against apoL1 peptide.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "SRA" refers to serum resistance-associated protein from *Trypanosoma brucei rhodesiense*. The amino acid sequence of full-length SRA is provided in GenBank as accession number CAA85518.2 and is also referred to herein as SEQ ID NO: 289. SRA is also found in GenBank as accession number AAC72381.1 and partial sequences of SRA as accession numbers CAD90580.1 and CAC87890.1. The term "SRA" also includes protein variants of SRA having the amino acid sequence of SEQ ID NOs: 290, 291, 292, 293, 294, 295 or 296. The term "SRA" includes recombinant SRA or a fragment thereof as exemplified by SEQ ID NO: 290. The term also encompasses SRA or a fragment thereof coupled to, for example, histidine tag, mouse or human Fc, or a signal sequence such as ROR1. For example, the term includes sequences exemplified by SEQ ID NOs: 291, 292 or 293, comprising mROR1 signal sequence (aa 1-29) at the N-terminal, and histidine tag or mouse Fc (mIgG2a) or human Fc (hIgG1) at the C-terminal, coupled to amino acid residues 29-274 of full-length SRA. Protein variants as exemplified by SEQ ID NOs: 294, 295 and 296 comprise mROR1 signal sequence (aa 1-29) at the N-terminal, and histidine tag or mouse Fc (mIgG2a) or human Fc (hIgG1) at the C-terminal, coupled to amino acid residues 29-388 of full length SRA.

SRA is a member of variant surface glycoprotein (VSG) family of trypanosomes. VSG covers the entire plasma membrane of the parasite. SRA is a protein of 410 amino acids with a long N-terminal hairpin that contains two amphipathic alpha-helices (Pays et al 2006, Nature Rev. Microbiol. 4: 477-486). The SRA gene is only found in *T. brucei rhodesiense* and SRA protein is expressed only in *T. brucei rhodesiense* variants which are resistant to human (or primate) serum. *T. brucei rhodesiense* variants which do not express SRA are sensitive to the trypanolytic factor or apolipoprotein L1 (apoL1) present in human or primate serum.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region (CO. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-SRA monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-SRA monoclonal antibodies comprising variants of any of the HCVR, LCVR, and/or CDR amino acid sequences disclosed herein having one or more conservative substitutions. For example, the present invention includes anti-SRA antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germ line immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-9}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to SRA. Moreover, multi-specific antibodies that bind to one domain in SRA and one or more additional antigens or a bi-specific that binds to two different regions of SRA are nonetheless considered antibodies that "specifically bind", as used herein.

The term "high affinity" antibody refers to those mAbs having a binding affinity to SRA, expressed as $K_D$, of at least $10^{-8}$ M; preferably $10^{-9}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from SRA, with a rate constant of $1\times10^{-3}$ s$^{-1}$ or less, preferably $1\times10^{-4}$ s$^{-1}$ or less, as determined by surface plasmon resonance, e.g., BIACORE™

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to SRA.

In specific embodiments, antibody or antibody fragments of the invention may be conjugated to a moiety such a ligand or a therapeutic moiety ("immunoconjugate"), such as an antibiotic, a second anti-SRA antibody, or an antibody to any other trypanosomal antigen, or an immunotoxin, or any other therapeutic moiety useful for treating a disease or condition including sleeping sickness.

An "isolated antibody", as used herein, is intended to refer to an antibody that is substantially free of other antibodies (Abs) having different antigenic specificities (e.g., an isolated antibody that specifically binds SRA, or a fragment thereof, is substantially free of Abs that specifically bind antigens other than SRA.

A "blocking antibody" or a "neutralizing antibody", as used herein (or an "antibody that neutralizes SRA activity"), is intended to refer to an antibody whose binding to SRA results in inhibition of at least one biological activity of SRA. For example, an antibody of the invention may prevent SRA binding to apoL1, preferably at about pH 4.5.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

In specific embodiments, the antibody or antibody fragment for use in the method of the invention may be mono-specific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second C$_H$3 include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "sleeping sickness", as used herein, refers to human African trypanosomiasis caused by two subspecies of the protozoan flagellate *Trypanosoma brucei*, namely *T. brucei gambiense* and *T. brucei rhodesiense*. *T. brucei rhodesiense* causes the acute and severe form of sleeping sickness, also called the East African sleeping sickness. It is a lethal infection transmitted by tsetse flies in humans and in cattle and other domestic and wild animals. Sleeping sickness is characterized by fever, headache, joint pain and lymphadenopathy, among other symptoms, in the initial phase. The second phase of the disease is neurological wherein the parasite invades the central nervous system by crossing the blood-brain barrier and causes symptoms such as confusion and disruption of the sleep behavior. The trypanosomal parasite produces tryptophol, a sleep-inducing chemical in the host; hence the disease name. Without treatment, the disease is invariably fatal.

General Description

Humans are resistant to trypanosomal pathogens due to an innate immunity factor present in the human serum, the trypanosome lytic factor (TLF) which lyses the trypanosomal pathogens (Rifkin 1978, PNAS 75: 3450-3454). The TLF is a subset of high density lipoprotein (HDL) fraction in the human serum. The key trypanolytic component of TLF is apolipoprotein-L1 (apoL1). The other important components of TLF are apoA1 and haptoglobin-related protein (Hpr), which binds to free serum hemoglobin (Hb). Endocytosis of apoL1 containing HDL occurs via a receptor in the flagellar pocket that recognizes the Hpr-Hb dimer. (Vanhamme et al 2003, Nature 422: 83-87; Vanhollebeke et al 2007, PNAS 104: 4118-4123). The endocytosed apoL1-containing TLF is trafficked to the lysosome. ApoL1 contains an anion-selective membrane pore, similar to that of bacterial colicins. When inserted into the lysosomal membrane, this pore allows the influx of chloride ions into the lysosome, which triggers the simultaneous entry of water and uncontrolled swelling of the vacuole until the parasite dies (Perez-Morga, et al 2005, Science 309: 469-472).

However, *T. brucei gambiense* and *T. brucei rhodesiense* are resistant to human serum and thus cause human disease. In *T. brucei gambiense*, the resistance is due to reduced haptoglobin receptor expression on the trypanosomal cell (Kieft et al 2010, PNAS 107: 16137-16141). *T. brucei rhodesiense* produces serum resistance-associated (SRA) protein which prevents the action of apoL1 (Degreef & Hamers 1994, Mol. Biochem. Parasitol. 68: 277-284). SRA is a variant of the variant surface glycoprotein (VSG) which forms the surface coat of the trypanosomal cell. SRA has been localized predominantly to the endosome; however presence of SRA on the surface or in the flagellar pocket cannot be ruled out (Vanhamme 2010, Infectious Disorders—Drug Targets 10: 266-282). SRA binds to apoL1 in the endosome and prevents the apoL1 action in the lysosome, thus protecting the trypanosome from lysis.

There is no vaccine available for sleeping sickness due to the ability of *T. brucei rhodesiense* to change its surface coat antigens. The drugs currently used such as suramin and melarsoprol have severe side effects such as neurotoxicity, renal failure and reactive encephalopathy. Thus, there is an unmet need to develop new effective therapy with less severe side effects for sleeping sickness.

The antibodies described herein bind to SRA at neutral pH and can remain bound to and block the interaction of SRA with apoL1 through pH 4.5. Blocking the interaction of SRA makes apoL1 available for interaction with the lysosome where it causes osmotic swelling and rupture thus killing the trypanosome. The antibodies described herein block SRA binding to apoL1 at lysosomal pH (pH 4.5).

The antibodies described herein demonstrate specific binding to SRA and in some embodiments, may be useful for treating patients suffering from sleeping sickness. The antibodies when administered to a subject suffering from sleeping sickness may reduce the infection by *T. brucei rhodesiense* in the subject. They may be used to inhibit the growth of or lyse *T. brucei rhodesiense* in a subject. They may be used alone or as adjunct therapy with other therapeutic moieties or modalities known in the art for treating sleeping sickness.

In certain embodiments, the antibodies of the invention are obtained from mice immunized with a primary immunogen, such as a full length SRA [See GenBank accession number CAA85518.2 (SEQ ID NO: 289)] or with a recombinant form of SRA (SEQ ID NO: 290) or modified SRA fragments (SEQ ID NOS: 291-296), followed by immunization with a secondary immunogen, or with an immunogenically active fragment of SRA.

The immunogen may be a biologically active and/or immunogenic fragment of SRA or DNA encoding the active fragment thereof. The fragment may be derived from the N-terminal or C-terminal domain of SRA. In certain embodiments of the invention, the immunogen is a fragment of SRA that ranges from amino acid residues 29-274 of SEQ ID NO: 289.

The full-length amino acid sequence of full length SRA is shown as SEQ ID NO: 289.

In certain embodiments, antibodies that bind specifically to SRA may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of SRA specific antibodies. In certain embodiments, any one or more of the above-noted regions of SRA, or fragments thereof may be used for preparing monospecific, bispecific, or multispecific antibodies.

Anti-SRA Antibodies with a Broad pH Range

The present invention provides antibodies and antigen-binding fragments thereof that exhibit binding to SRA at a broad range of pH. The antibodies of the invention bind to SRA at a pH ranging from neutral pH to acidic pH.

As used herein, the expression "acidic pH" means a pH of 6.0 or less. The expression "acidic pH" includes pH values of about 6.0, 5.9, 5.8, 5.7, 5.6, 5.5, 5.4, 5.3, 5.2, 5.1, 5.0, 4.9, 4.8, 4.7, 4.6, 4.5 or less.

As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

The binding properties of an antibody for a particular antigen may be expressed in terms of the $k_d$ of the antibody. The $k_d$ of an antibody refers to the dissociation rate constant of the antibody with respect to a particular antigen and is expressed in terms of reciprocal seconds (i.e., $sec^{-1}$). The present invention includes antibodies that bind SRA with $k_d$ value less than about $1.7 \times 10^{-2}$ at both acidic and neutral pH.

The binding properties of an antibody for a particular antigen may also be expressed in terms of the t½ of the antibody. The t½ of an antibody refers to the half-life of the antibody-antigen interaction. In certain embodiments, the invention includes antibodies with a t½ of more than about 0.5 minutes to about 290 minutes at both acidic and neutral pH.

$K_D$ values, $k_d$ values, and t½ times, as expressed herein, may be determined using a surface plasmon resonance-based biosensor to characterize antibody-antigen interactions. (See Example 5, herein). $K_D$ values, $k_d$ values, and t½ times can be determined at 25° C. or 37° C.

It has been discovered that binding of the antibodies to SRA at neutral and acidic pH may impart desirable/improved biological properties to the antibodies as compared to antibodies that bind to SRA only at neutral pH. Antibodies that bind to SRA at acidic pH may be routed to the lysosome in the trypanosomal parasite and therefore may prevent SRA binding to the trypanolytic protein apoL1. In certain embodiments of the invention, the antibodies that bind to SRA at acidic pH block or prevent SRA binding to apoL1 at acidic pH.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to SRA. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_{H1}$-$C_H$2, (V) $V_H$-$C_{H1}$-$C_{H2}$-$C_H$3, $V_H$-$C_{H2}$-$C_H$3; $V_H$-$C_L$; (viii) $V_L$-$C_H$1; (ix) $V_L$-$C_H$2, (x) $V_L$-$C_H$3; (xi)$_{VL}$-$C_{H1}$-$C_H$2; (xii) $V_L$-$C_{H1}$-$C_{H2}$-$C_H$3; (xiii) $V_L$-$C_{H2}$-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to SRA.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to SRA are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-10}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-SRA antibodies and antibody fragments of the present invention encompass proteins having amino acid sequences that vary from those of the described antibodies, but that retain the ability to bind SRA. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-SRA Antibodies Comprising Fc Variants

According to certain embodiments of the present invention, anti-SRA antibodies are provided comprising an Fc domain comprising one or more mutations which enhance or diminish antibody binding to the FcRn receptor, e.g., at acidic pH as compared to neutral pH. For example, the present invention includes anti-SRA antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-SRA antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-SRA antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention may function by binding to SRA. In some embodiments, the antibodies of the present invention may bind to either the apoL1-binding domain or outside the apoL1-binding domain of SRA, or to a fragment of either domain. In some embodiments, the antibodies of the present invention may bind to more than one domain (cross-reactive antibodies).

In certain embodiments, the antibodies of the present invention may bind to an epitope located in the apoL1 binding domain comprising amino acid residues 202-222 of SRA (SEQ ID NO: 289). In one embodiment, the antibodies may bind to an epitope comprising one or more amino acids selected from the group consisting of amino acid residues 174-194 of SEQ ID NO: 290.

In certain embodiments, the antibodies of the present invention may function by blocking or inhibiting the apoL1-binding activity associated with SRA by binding to any other region or fragment of the full length protein, the amino acid sequence of which is shown in SEQ ID NO: 289. In certain embodiments, the antibodies may attenuate or modulate the interaction between SRA and apoL1.

In certain embodiments, the antibodies of the present invention may be bi-specific antibodies. The bi-specific antibodies of the invention may bind one epitope in one domain and may also bind one epitope in a second domain of SRA. In certain embodiments, the bi-specific antibodies of the invention may bind two different epitopes in the same domain.

In certain embodiments, the antibodies of the present invention bind to SRA at a pH ranging from acidic to neutral pH. In certain embodiments, the antibodies bind to SRA at a pH ranging from about 7.4 to about 4.5. In some embodiments, the antibodies of the present invention remain bound to SRA from pH 7.4 through pH 4.5. It is believed that antibodies able to bind to SRA at acidic pH may be routed to the lysosome for degradation and may be able to block SRA binding to the trypanolytic protein apoL1 in the trypanosomal cell. As illustrated by the Examples herein, the antibodies binding to SRA at acidic pH are able to block SRA binding to apoL1. In some embodiments, the antibodies of the present invention block SRA binding to apoL1 at pH 4.5.

In one embodiment, the invention provides a fully human monoclonal antibody or antigen-binding fragment thereof that binds to SRA, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 286, or a substantially similar sequence thereof having at least 90%, at least 95%, at least 98% or at least 99% sequence identity; (v) binds to SRA with a $K_D$ equal to or less than $10^{-10}$; and (vi) binds to SRA at pH 7.4 and remains bound through pH 4.5.

In one embodiment, the invention provides a fully human monoclonal antibody or antigen-binding fragment thereof that blocks SRA binding to apoL1, wherein the antibody or fragment thereof exhibits one or more of the following characteristics: (i) comprises a HCVR having an amino acid sequence selected from the group consisting of SEQ ID NO: 66, 98, 130, 146, 162, 210, 226, 242, 258, and 274, or a substantially similar sequence thereof having at least 90%, at least 95%, at least 98% or at least 99% sequence identity; (ii) comprises a LCVR having an amino acid sequence selected from the group consisting of SEQ ID NO: 74, 106, 138, 154, 170, 218, 234, 250, 266, and 282, or a substantially similar sequence thereof having at least 90%, at least 95%, at least 98% or at least 99% sequence identity; (iii) comprises a HCDR3 domain having an amino acid sequence selected from the group consisting of SEQ ID NO: 72, 104, 136, 152, 168, 216, 232, 248, 264, and 280, or a substantially similar sequence thereof having at least 90%, at least 95%, at least 98% or at least 99% sequence identity; and a LCDR3 domain having an amino acid sequence selected from the group consisting of SEQ ID NO: 80, 112, 144, 160, 176, 224, 240, 256, 272, and 288, or a substantially similar sequence thereof having at least 90%, at least 95%, at least 98% or at least 99% sequence identity; (iv) comprises a HCDR1 domain having an amino acid sequence selected from the group consisting of SEQ ID NO: 68, 100, 132, 148, 164, 212, 228, 244, 260, and 276, or a substantially similar sequence thereof having at least 90%, at least 95%, at least 98% or at least 99% sequence identity; a HCDR2 domain having an amino acid sequence selected from the group consisting of SEQ ID NO: 70, 102, 134, 150, 166, 214, 230, 246, 262, and 278, or a substantially similar sequence thereof having at least 90%, at least 95%, at least 98% or at least 99% sequence identity; a LCDR1 domain having an amino acid sequence selected from the group consisting of SEQ ID NO: 76, 108, 140, 156, 172, 220, 236, 252, 268, and 284, or a substantially similar sequence thereof having at least 90%, at least 95%, at least 98% or at least 99% sequence identity; and a LCDR2 domain having an amino acid sequence selected from the group consisting of SEQ ID NO: 78, 110, 142, 158, 174, 222, 238, 254, 270, and 286, or a substantially similar sequence thereof having at least 90%, at least 95%, at least 98% or at least 99% sequence identity; (v) demonstrates a $K_D$ equal to or less than $10^{-10}$; (vi) binds to SRA at pH ranging from about 7.4 to about 4.5; and (vii) blocks binding of SRA to apoL1.

Certain anti-SRA antibodies of the present invention are able to bind to and neutralize the activity of SRA, as determined by in vitro or in vivo assays. The ability of the antibodies of the invention to bind to and neutralize the activity of SRA may be measured using any standard method known to those skilled in the art, including binding assays, or activity assays, as described herein.

Non-limiting, exemplary in vitro assays for measuring binding activity are illustrated in Examples 5, 6 and 7, herein. In Example 5, the binding affinities and kinetic constants of human anti-SRA antibodies were determined by surface plasmon resonance and the measurements were conducted on a T200 Biacore instrument. In Example 6, blocking assays were used to determine the ability of the anti-SRA antibodies to block apoL1-binding ability of SRA in vitro. In Example 7, blocking assays were used to determine cross-competition between anti-SRA antibodies.

In certain embodiments, the antibodies of the present invention are able to inhibit the growth and activity of the trypanosomal parasites in vitro and in a subject infected with *T. brucei rhodesiense*. Example 8 describes the trypanolytic activity of the anti-SRA antibodies in an in vitro assay. Example 9 describes the activity of the anti-SRA antibodies in mice models in protecting against infection by *T. brucei rhodesiense*.

The present invention includes anti-SRA antibodies and antigen binding fragments thereof which bind to at least one biologically active fragment of any of the following proteins, or peptides: full length SRA (SEQ ID NO: 289), and various recombinant forms of SRA (SEQ ID NOS: 290-296). Any of the SRA peptides described herein, or fragments thereof, may be used to generate anti-SRA antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. Other sequences include mouse IgG2a or human IgG1 used to tag C-terminal end of the peptide or mROR1 signal sequence for N-terminal tagging.

The antibodies specific for SRA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Epitope Mapping and Related Technologies

The present invention includes anti-SRA antibodies which interact with one or more amino acids found within one or more domains of the SRA molecule including, e.g., the apoL1-binding domain comprising amino acid residues 202-222 of SRA. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the SRA molecule (e.g. a linear epitope in a domain). Alternatively, the epitope may consist of a plurality of non-contiguous amino acids (or amino acid sequences) located within either or both of the aforementioned domains of the SRA molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-SRA antibodies or antigen-binding fragments thereof bind an epitope within any one or more of the regions exemplified in SRA, either in natural form, as exemplified in SEQ ID NO: 289, or recombinantly produced, as exemplified in SEQ ID NOS: 290-296, or to a fragment thereof. In some embodiments, the antibodies of the invention bind to an apoL1 binding epitope region comprising one or more amino acids selected from the group consisting of amino acid residues 202-222 of SRA.

In certain embodiments, the antibodies of the invention, as shown in Table 1, interact with at least one amino acid sequence selected from the group consisting of amino acid residues ranging from about position 31 to about position 174 of SEQ ID NO: 289; amino acid residues ranging from about position 174 to about position 194 of SEQ ID NO: 289; or amino acid residues ranging from about position 194 to about position 274 of SEQ ID NO: 289. These regions are partially exemplified in SEQ ID NOs: 290-296.

The present invention includes anti-SRA antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-SRA antibodies that compete for binding to SRA or a SRA fragment with any of the specific exemplary antibodies described herein in Table 1, or an antibody having the CDR sequences of any of the exemplary antibodies described in Table 1.

One can easily determine whether an antibody binds to the same epitope as, or competes for binding with, a reference anti-SRA antibody by using routine methods known in the art. For example, to determine if a test antibody binds to the same epitope as a reference anti-SRA antibody of the invention, the reference antibody is allowed to bind to a SRA protein or peptide under saturating conditions. Next, the ability of a test antibody to bind to the SRA molecule is assessed. If the test antibody is able to bind to SRA following saturation binding with the reference anti-SRA antibody, it can be concluded that the test antibody binds to a different epitope than the reference anti-SRA antibody. On the other hand, if the test antibody is not able to bind to the SRA protein following saturation binding with the reference anti-SRA antibody, then the test antibody may bind to the same epitope as the epitope bound by the reference anti-SRA antibody of the invention.

To determine if an antibody competes for binding with a reference anti-SRA antibody, the above-described binding methodology is performed in two orientations: In a first orientation, the reference antibody is allowed to bind to a SRA protein under saturating conditions followed by assessment of binding of the test antibody to the SRA molecule. In a second orientation, the test antibody is allowed to bind to a SRA molecule under saturating conditions followed by assessment of binding of the reference antibody to the SRA molecule. If, in both orientations, only the first (saturating) antibody is capable of binding to the SRA molecule, then it is concluded that the test antibody and the reference antibody compete for binding to SRA. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-SRA monoclonal antibody conjugated to a therapeutic moiety ("immunoconjugate"), such as a trypanocidal or trypanostatic agent to treat sleeping sickness. As used herein, the term "immunoconjugate" refers to an antibody which is chemically or biologically linked to a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to SRA. In certain embodiments, the antibody may be conjugated to apoL1 or a fragment thereof or to Hpr or a component of TLF. The type of therapeutic moiety that may be conjugated to the anti-SRA antibody and will take into account the condition to be treated and the desired therapeutic effect to be achieved. Examples of suitable agents for forming immunoconjugates are known in the art; see for example, WO 05/103081.

Multi-specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for the apoL1-binding domain of SRA, or a fragment thereof, and the other arm of the immunoglobulin is specific for binding outside the apoL1-binding domain of SRA, or a second therapeutic target, or is conjugated to a therapeutic moiety. In certain embodiments of the invention, one arm of an immunoglobulin is specific for an epitope comprising amino acid residues 174-194 of SRA (SEQ ID NO: 290) or a fragment thereof, and the other arm of the immunoglobulin is specific for another epitope of SRA, or a fragment thereof.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

Therapeutic Administration and Formulations

The invention provides therapeutic compositions comprising the anti-SRA antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating sleeping sickness in an adult patient, or for preventing sleeping sickness, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/ 2009/439389), incorporated herein by reference. Nanoparticles may be developed and conjugated to antibodies contained in pharmaceutical compositions to target parasites. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 100 mg and in about 10 to about 250 mg for the other dosage forms.

Therapeutic Uses of the Antibodies

In some embodiments of the invention, the antibodies described herein are useful for treating subjects suffering from African sleeping sickness. The antibodies may be used to treat early stage or late-stage symptoms of sleeping sickness. Common symptoms of the early stage of sleeping sickness include, but are not limited to, fever, headaches, joint pain, itching, severe swelling of the lymph nodes, anemia, weight loss, fatigue, cardiac features such as myocarditis, pericarditis and congestive cardiac failure, and endocrine or kidney dysfunction.

The antibodies of the invention may be used to treat patients of sleeping sickness for their neurological symptoms and features seen in a later stage of the infection. In some embodiments, the antibodies of the present invention may be administered to patients suffering from the later stage of sleeping sickness with symptoms such as confusion, reduced co-ordination, and disruption of the sleep cycle with bouts of fatigue punctuated by manic periods leading to daytime slumber and night-time insomnia, and a rapid mental deterioration leading to coma and death. One or more antibodies of the present invention may be administered to relieve or prevent or decrease the severity of one or more of the symptoms or conditions above. In one embodiment, the antibodies of the present invention may be used to facilitate lysis of the infecting trypanocytes and thereby prevent parasitemia in a subject.

It is also contemplated herein to use one or more antibodies of the present invention prophylactically to patients at risk for developing sleeping sickness. For example, the antibodies may be administered to visitors to safari parks in Africa, or native people at risk of being bitten by tsetse flies in endemic areas. In one embodiment, the antibodies may be administered to a subject who is bitten by tsetse flies to prevent infection by the trypanosomal parasite.

In a further embodiment of the invention the present antibodies are used for the preparation of a pharmaceutical composition for treating patients suffering from sleeping sickness. In another embodiment of the invention the present antibodies are used as adjunct therapy with any other agent useful for treating sleeping sickness, or any other therapy known to those skilled in the art.

Combination Therapies

Combination therapies may include an anti-SRA antibody of the invention and any additional therapeutic agent that may be advantageously combined with an antibody of the invention, or with a biologically active fragment of an antibody of the invention.

The antibodies of the present invention may be combined synergistically with one or more anti-trypanosomal drugs used to treat sleeping sickness. Examples of anti-trypanosomal drugs are melarsoprol, suramin, eflornithine and nifurtimox. In some embodiments, one or more antibodies of the present invention may be used in combination with a NSAID, another antibody to SRA, an antibody to another trypanosomal protein such as VSG, a recombinant therapeutic, a dietary supplement or any palliative care to treat sleeping sickness. In one embodiment, the antibodies of the present invention may be combined with a recombinant therapeutic such as a recombinant form of the apoL1 protein (see, for example, Baral et al 2006, Nature Med. 12: 580-584; or U.S. Pat. No. 7,585,511).

The additional therapeutically active component(s) may be administered prior to, concurrent with, or after the administration of the anti-SRA antibody of the present invention. For purposes of the present disclosure, such administration regimens are considered the administration of an anti-SRA antibody "in combination with" a second therapeutically active component.

Diagnostic Uses of the Antibodies

The anti-SRA antibodies of the present invention may be used to detect and/or measure SRA in a sample, e.g., for diagnostic purposes. Some embodiments contemplate the use of one or more antibodies of the present invention in assays to detect sleeping sickness. For example, the antibodies may be used to detect sleeping sickness or infection by *T. brucei* rhodesiense in a subject bitten by tsetse flies. Exemplary diagnostic assays for SRA may comprise, e.g., contacting a sample, obtained from a patient, with an anti-SRA antibody of the invention, wherein the anti-SRA antibody is labeled with a detectable label or reporter molecule or used as a capture ligand to selectively isolate SRA from patient samples. Alternatively, an unlabeled anti-SRA antibody can be used in diagnostic applications in combination with a secondary antibody which is itself detectably labeled. The detectable label or reporter molecule can be a radioisotope, such as 3H, $^{14}C$, $^{32}P$, $^{33}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure SRA in a sample include enzyme-linked immunosorbent assay (ELISA), radioimmunoassay (RIA), and fluorescence-activated cell sorting (FACS).

Samples that can be used in SRA diagnostic assays according to the present invention include any tissue or fluid sample obtainable from a patient, which contains detectable quantities of either SRA protein, or fragments thereof, under normal or pathological conditions. Generally, levels of SRA in a particular sample obtained from a healthy patient (e.g., a patient not afflicted with sleeping sickness) will be measured to initially establish a baseline, or standard, level of SRA. This baseline level of SRA can then be compared against the levels of SRA measured in samples obtained from individuals suspected of having sleeping sickness-related condition, or symptoms associated with such condition.

The antibodies specific for SRA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antibodies as markers for predicting prognosis of sleeping sickness in patients. Antibodies of the present invention may be used in diagnostic assays to evaluate prognosis of sleeping sickness in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to SRA

An immunogen comprising any one of the following can be used to generate antibodies to SRA. In certain embodiments, the antibodies of the invention are obtained from mice immunized with a full length, native SRA (See GenBank accession number CAA85518.2) (SEQ ID NO: 289), or with a recombinant SRA peptide (SEQ ID NO: 290). Alternatively, SRA or a fragment thereof may be produced using standard biochemical techniques and modified (SEQ ID NOS: 291-296) and used as immunogen.

In certain embodiments, the immunogen may be a peptide from the N terminal or C terminal end of SRA. In certain embodiments of the invention, the immunogen is a fragment of SRA that ranges from about amino acid residues 29-274 of SEQ ID NO: 289.

In some embodiments, the immunogen may be a recombinant SRA peptide expressed in *E. coli* or in any other eukaryotic or mammalian cells such as Chinese hamster ovary (CHO) cells.

In certain embodiments, antibodies that bind specifically to SRA may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of SRA specific antibodies. In certain embodiments, any one or more of the above-noted domains of SRA, or fragments thereof may be used for preparing monospecific, bispecific, or multispecific antibodies (see Example 10 below for details).

The full length proteins, or fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a SRA-specific immunoassay. When a desired immune response was achieved splenocytes were harvested and fused with mouse myeloma cells to preserve their viability and form hybridoma cell lines. The hybridoma cell lines were screened and selected to identify cell lines that produce SRA-specific antibodies. Using this technique, and the various immunogens described above, several anti-SRA, as well as cross-reactive, chimeric antibodies (i.e., antibodies possessing human variable domains and mouse constant domains) were obtained; exemplary antibodies generated in this manner were designated as H2aM10200N, H2aM10204N, H2bM10093N, H2aM10285N, H2aM10201N, H2aM10095N, H2aM10207N, H2aM10288N, H2aM10293N, H2aM10094N, H2aM10289N, H2aM10202N, H2aM10208N, H2bM10205N, H2bM10203N, H2bM10206N, H2aM10291N, H2aM10297N, H2aM10295N, H2aM10092N, H2aM10290N, H2aM10292N, H1M10096N, H2bM10097N, H2aM10294N, and H2aM10296N.

Anti-SRA antibodies were also isolated directly from antigen-positive B cells without fusion to myeloma cells, as described in U.S. 2007/0280945A1, herein specifically incorporated by reference in its entirety. Using this method, several fully human anti-SRA antibodies (i.e., antibodies possessing human variable domains and human constant domains) were obtained; exemplary antibodies generated in this manner were designated as follows: H1H10026P, H1H10027P, H1H10031P, H1H10040P, H1H10041P, H1H10045P, H1H10056P, H1H10058P, H1H10059P, H1H10061P, H1H10064P, H1H10067P, and H1H10069P.

The biological properties of the exemplary antibodies generated in accordance with the methods of this Example are described in detail in the Examples set forth below.

Example 2

Heavy and Light Chain Variable Region Amino Acid Sequences

Table 1 sets forth the amino acid sequence identifiers of the heavy and light chain variable regions and CDRs of selected anti-SRA antibodies of the invention. The corresponding nucleic acid sequence identifiers are set forth in Table 2.

Antibodies are typically referred to herein according to the following nomenclature: Fc prefix (e.g. "H4H", "H1M", "H2M"), followed by a numerical identifier (e.g. "10064" as shown in Table 1), followed by a "P" or "N" suffix. Thus, according to this nomenclature, an antibody may be referred to as, e.g. "H1H10064". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H10026P | 2 | 4 | 6 | 8 | 10 | 12 | 14 | 16 |
| H1H10027P | 18 | 20 | 22 | 24 | 26 | 28 | 30 | 32 |
| H1H10031P | 34 | 36 | 38 | 40 | 42 | 44 | 46 | 48 |
| H1H10040P | 50 | 52 | 54 | 56 | 58 | 60 | 62 | 64 |
| H1H10041P | 66 | 68 | 70 | 72 | 74 | 76 | 78 | 80 |
| H1H10045P | 82 | 84 | 86 | 88 | 90 | 92 | 94 | 96 |
| H1H10056P | 98 | 100 | 102 | 104 | 106 | 108 | 110 | 112 |

TABLE 1-continued

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H10058P | 114 | 116 | 118 | 120 | 122 | 124 | 126 | 128 |
| H1H10059P | 130 | 132 | 134 | 136 | 138 | 140 | 142 | 144 |
| H1H10061P | 146 | 148 | 150 | 152 | 154 | 156 | 158 | 160 |
| H1H10064P | 162 | 164 | 166 | 168 | 170 | 172 | 174 | 176 |
| H1H10067P | 178 | 180 | 182 | 184 | 186 | 188 | 190 | 192 |
| H1H10069P | 194 | 196 | 198 | 200 | 202 | 204 | 206 | 208 |
| H2M10093N | 210 | 212 | 214 | 216 | 218 | 220 | 222 | 224 |
| H2M10200N | 226 | 228 | 230 | 232 | 234 | 236 | 238 | 240 |
| H2M10201N | 242 | 244 | 246 | 248 | 250 | 252 | 254 | 256 |
| H2M10204N | 258 | 260 | 262 | 264 | 266 | 268 | 270 | 272 |
| H2M10285N | 274 | 276 | 278 | 280 | 282 | 284 | 286 | 288 |

TABLE 2

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H10026P | 1 | 3 | 5 | 7 | 9 | 11 | 13 | 15 |
| H1H10027P | 17 | 19 | 21 | 23 | 25 | 27 | 29 | 31 |
| H1H10031P | 33 | 35 | 37 | 39 | 41 | 43 | 45 | 47 |
| H1H10040P | 49 | 51 | 53 | 55 | 57 | 59 | 61 | 63 |
| H1H10041P | 65 | 67 | 69 | 71 | 73 | 75 | 77 | 79 |
| H1H10045P | 81 | 83 | 85 | 87 | 89 | 91 | 93 | 95 |
| H1H10056P | 97 | 99 | 101 | 103 | 105 | 107 | 109 | 111 |
| H1H10058P | 113 | 115 | 117 | 119 | 121 | 123 | 125 | 127 |
| H1H10059P | 129 | 131 | 133 | 135 | 137 | 139 | 141 | 143 |
| H1H10061P | 145 | 147 | 149 | 151 | 153 | 155 | 157 | 159 |
| H1H10064P | 161 | 163 | 165 | 167 | 169 | 171 | 173 | 175 |
| H1H10067P | 177 | 179 | 181 | 183 | 185 | 187 | 189 | 191 |
| H1H10069P | 193 | 195 | 197 | 199 | 201 | 203 | 205 | 207 |
| H2M10093N | 209 | 211 | 213 | 215 | 217 | 219 | 221 | 223 |
| H2M10200N | 225 | 227 | 229 | 231 | 233 | 235 | 237 | 239 |
| H2M10201N | 241 | 243 | 245 | 247 | 249 | 251 | 253 | 255 |
| H2M10204N | 257 | 259 | 261 | 263 | 265 | 267 | 269 | 271 |
| H2M10285N | 273 | 275 | 277 | 279 | 281 | 282 | 285 | 287 |

Example 3

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 3 sets forth the gene usage for selected antibodies in accordance with the invention.

TABLE 3

| Antibody Identifier | | HCVR | | | LCVR | |
|---|---|---|---|---|---|---|
| Antibody | HCVR/LCVR | $V_H$ | $D_H$ | $J_H$ | $V_K$ | $J_K$ |
| H1H10026P | 2/10 | 3-30 | D1-7 | 4 | 3-20 | 4 |
| H1H10027P | 18/26 | 3-9 | D3-10 | 3 | 1-5 | 4 |
| H1H10031P | 34/42 | 3-20 | D3-16 | 6 | 1-17 | 1 |
| H1H10040P | 50/58 | 3-33 | D5-18 | 4 | 1-12 | 4 |
| H1H10041P | 66/74 | 1-69 | D3-16 | 4 | 1-6 | 2 |
| H1H10045P | 82/90 | 3-33 | D5-18 | 4 | 1-12 | 3 |
| H1H10056P | 98/106 | 3-30 | D1-7 | 4 | 3-20 | 1 |
| H1H10058P | 114/122 | 3-7 | D3-10 | 5 | 4-1 | 1 |
| H1H10059P | 130/138 | 1-2 | D1-1 | 4 | 2-24 | 1 |

TABLE 3-continued

| Antibody Identifier | | HCVR | | | LCVR | |
|---|---|---|---|---|---|---|
| Antibody | HCVR/LCVR | $V_H$ | $D_H$ | $J_H$ | $V_K$ | $J_K$ |
| H1H10061P | 146/154 | 3-30 | D3-10 | 6 | 4-1 | 4 |
| H1H10064P | 162/170 | 1-69 | None identified | 3 | 1-17 | 2 |
| H1H10067P | 178/186 | 4-31 | D7-27 | 6 | 1-5 | 2 |
| H1H10069P | 194/202 | 4-59 | None identified | 4 | 1-5 | 4 |
| H2M10093N | 210/218 | 3-21 | D1-1 | 4 | 1-12 | 3 |
| H2M10200N | 226/234 | 1-69 | D5-12 | 4 | 1-6 | 1 |
| H2M10201N | 242/250 | 3-30 | D1-7 | 4 | 3-20 | 4 |
| H2M10204N | 258/266 | 1-69 | D5-12 | 4 | 1-6 | 1 |
| H2M10285N | 274/282 | 1-69 | D5-12 | 4 | 1-6 | 1 |

Example 4

H/DX Epitope Mapping of SRA Against apoL1 Peptide

H/DX epitope mapping of SRA against apoL1 peptide was essentially carried out as per the protocol shown in FIG. 1. Prior to H/D exchange experiment, both SRA (SEQ ID NO: 290) and apoL1 peptides (SEQ ID NO: 297) were buffer-exchanged into citrate solution (0.02 M citric acid/NaOH, pH 5.0, 0.15 M NaCl) with a concentration of 4.0 mg/ml and 1.5 mg/ml respectively. H/D exchange was initiated by mixing 1 µl SRA alone or 1 µl SRA-apoL1 complex (molar ratio: 1:3) with 9 µl pH 5.0 Citrate buffer prepared in D₂O. The deuteration periods were 1 min, 5 min, and 10 min. The control or 0 min deuteration was SRA or SRA-apoL1 complex diluted into pH 5.0 citrate prepared in H₂O. The H/D reaction was then quenched by adding 190 µl ice-cold citrate buffer (0.05 M, pH 2.4). Following digestion with immobilized pepsin (Cat #20343) for 4 min at 4° C., the resulting peptides were desalted using ZipTip C18 chromatographic pipette tips and immediately analyzed by UltrafleXtreme matrix assisted laser desorption ionization time of flight (MALDI-TOF)-TO mass spectrometry. The centroid values or average mass-to-charge ratio (m/z) of all the detected peptides were calculated and compared to the control to determine the deuteration for different incubation periods.

Table 4 is a summary of deuteration difference between SRA alone and SRA complexed with apoL1 for all the peptides detected in the H/D exchange experiment. For 1 minute deuteration, three peptides covering residues 174-194 of SRA (SEQ ID NO: 290) were deuterated prominently less in the presence of apoL1 whereas all the other peptides had similar deuteration. For 5 min and 10 min deuteration, the region was also consistently deuterated less as compared with SRA alone. Therefore, this segment is defined by the H/D exchange method as a likely binding/epitope region of SRA for apoL1.

determined using a real-time surface plasmon resonance biosensor (Biacore T200) assay at 25° C.

Equilibrium dissociation constants ($K_D$) values for SRA binding to selected purified anti-SRA monoclonal antibodies were determined using a real-time surface plasmon resonance biosensor assay on a Biacore T200 instrument. The Biacore CM4 sensor chip surface was either derivatized with polyclonal rabbit anti-mouse antibody (GE Catalog# BR-1008-38) or with polyclonal goat anti-human Fc antibody (Jackson ImmunoResearch Laboratories, Inc Catalog#109-005-098); in order to capture around 100-350 RUs of anti-SRA monoclonal antibodies which were expressed with either a mouse Fc (AbPID prefix H1M, H2aM) or with human IgG1 Fc (AbPID prefix H1H) respectively. Kinetics of SRA binding to captured monoclonal antibody was performed at 25° C. in two different running buffers—pH 7.4 Citric/Phosphate buffer (9.1 mM Na2HPO4, 0.1 mM citric acid monohydrate, 2.5 mM KCl, 137 mM NaCl, 0.05% v/v Surfactant P20) and pH 4.5 Citric/Phosphate buffer (4.7 mM Na2HPO4, 5.3 mM citric acid monohydrate, 1.3 mM KCl, 137 mM NaCl, 0.05% v/v Surfactant P20). Different concentrations of SRA samples (SEQ ID NO: 290) were prepared in pH 7.4 buffer and were injected over the anti-SRA monoclonal antibody captured surface at a flow rate of 50 µl/min. SRA binding to the captured monoclonal antibodies was monitored for 4 min while the dissociation of mAb bound SRA was monitored for 7 min. Two different assays

TABLE 4

| Residues | MH+ | 1 min deuteration | | | 5 min deuteration | | | 10 min deuteration | | |
|---|---|---|---|---|---|---|---|---|---|---|
| | | SRA $m_t$-$m_0$ | SRA + apoL1 $m_t$-$m_0$ | Δ | SRA $m_t$-$m_0$ | SRA + apoL1 $m_t$-$m_0$ | Δ | SRA $m_t$-$m_0$ | SRA + apoL1 $m_t$-$m_0$ | Δ |
| 28-44 | 1800.00 | −0.02 | 0.11 | −0.13 | 0.22 | 0.34 | −0.12 | 0.32 | 0.32 | 0.00 |
| 28-47 | 2158.16 | 0.16 | 0.19 | −0.03 | 0.11 | 0.19 | −0.08 | 0.32 | 0.19 | 0.13 |
| 27-49 | 2485.38 | 0.19 | 0.17 | 0.02 | 0.47 | 0.17 | 0.30 | 0.69 | 0.23 | 0.46 |
| 28-49 | 2372.29 | 0.12 | 0.22 | −0.10 | 0.42 | 0.23 | 0.19 | 0.66 | 0.23 | 0.43 |
| 34-49 | 1718.92 | 0.18 | 0.25 | −0.07 | 0.37 | 0.15 | 0.22 | 0.55 | 0.21 | 0.34 |
| 132-144 | 1502.87 | 0.97 | 0.68 | 0.29 | 2.27 | 1.43 | 0.84 | 3.10 | 2.04 | 1.06 |
| 133-144 | 1403.83 | 0.14 | 0.21 | −0.07 | 0.98 | 0.38 | 0.60 | 1.98 | 1.00 | 0.98 |
| 134-144 | 1332.77 | 0.57 | 0.35 | 0.22 | 1.49 | 0.83 | 0.66 | 2.01 | 1.11 | 0.89 |
| 134-145 | 1461.81 | 0.35 | 0.44 | −0.09 | 1.47 | 0.74 | 0.73 | 2.06 | 1.41 | 0.64 |
| 158-173 | 1863.06 | 1.36 | 1.32 | 0.04 | 1.64 | 1.31 | 0.34 | 2.50 | 1.76 | 0.74 |
| 159-173 | 1734.01 | 1.3 | 1.21 | 0.09 | 1.76 | 1.21 | 0.54 | 2.20 | 1.20 | 1.00 |
| 159-174 | 1847.11 | 1.24 | 1.29 | −0.05 | 1.63 | 1.22 | 0.41 | 2.05 | 1.58 | 0.47 |
| 174-192 | 1981.13 | 3.32 | 2.71 | 0.61 | 5.27 | 4.11 | 1.16 | 5.84 | 4.50 | 1.34 |
| 174-194 | 2181.24 | 3.45 | 2.70 | 0.75 | 5.46 | 4.17 | 1.28 | 5.88 | 4.69 | 1.19 |
| 175-192 | 1868.05 | 3.29 | 2.54 | 0.75 | 4.96 | 3.88 | 1.09 | 5.38 | 4.17 | 1.21 |
| 224-246 | 2614.57 | 11.30 | 11.57 | −0.27 | 11.47 | 11.61 | −0.14 | 11.43 | 11.50 | −0.07 |
| 234-246 | 1558.98 | 5.70 | 5.85 | −0.15 | 5.90 | 5.95 | −0.04 | 5.74 | 6.00 | −0.26 |
| No ID | 2175.27 | 0.28 | 0.22 | 0.06 | 1.07 | 0.44 | 0.63 | 1.55 | 0.81 | 0.74 |

It is noteworthy that the deuteration for many other different regions was also noticeably reduced after 5 min or 10 min reaction in the presence of apoL1. This effect could be due to conformational change or allosteric effect upon binding apoL1.

Example 5

Antibody Binding to SRA as Determined by Surface Plasmon Resonance

Binding associative and dissociative rate constants ($k_a$ and $k_d$, respectively) and calculated equilibrium dissociation constants and dissociative half-lives ($K_D$ and $t_{1/2}$, respectively) for antigen binding to purified SRA antibodies were formats were adopted to characterize kinetics of SRA binding—(i) regular kinetics and (ii) pH 4.5 chase. Regular kinetics experiments were performed using pH 7.4 buffer as the running buffer and both the association and dissociation was performed in pH 7.4. For the chase format, association and dissociation were performed in pH 7.4 buffer and pH 4.5 buffer respectively.

Kinetic association ($k_a$) and dissociation ($k_d$) rate constants were determined by processing and fitting the data to a 1:1 binding model using Scrubber 2.0c curve fitting software. Only the dissociation rate (kd) was calculated for the pH 4.5 chase experiment. Binding dissociation equilibrium constants ($K_D$) and dissociative half-lives (t½) were calculated from the kinetic rate constants as:

$$K_D(M) = \frac{ka}{kd}, \text{ and } t^{1/2}(\min) = \frac{\ln(2)}{60 * kd}$$

Binding kinetics parameters for different anti-SRA monoclonal antibodies binding to different SRA reagents at 25° C. are shown in Table 5.

ImmunoResearch Laboratories, Inc Catalog#109-005-098); in order to, capture around 100-350 RUs of anti-SRA monoclonal antibodies which were expressed with either a mouse Fc (AbPID prefix H1M, H2aM) or with human IgG1 Fc (AbPID prefix H1H) respectively. The experiment was performed at 25° C. and pH 4.5 citric-phosphate buffer (4.7 mM Na2HPO4, TABLE 6-continued Subtraction of average background binding on Fc1

| mAb captured | Amount of mAb captured (RU) | 50 nM SRA binding (RU) | 50 nM SRA + 5 uM apoL1 peptide binding (RU) | 50 nM SRA + 5 uM mutant apoL1 peptide binding (RU) | % Blocking apoL1 peptide | % Blocking Mutant apoL1 peptide |
|---|---|---|---|---|---|---|
| H2bM10093N | 786 | 138 | 4 | 122 | 97 | 12 |
| H2aM10285N | 691 | 120 | 8 | 111 | 94 | 8 |
| H2aM10201N | 631 | 109 | 42 | 108 | 61 | 0 |
| H1H10064P | 365 | 76 | −11 | 67 | 100 | 11 |
| H1H10056P | 318 | 72 | −4 | 67 | 100 | 7 |
| H1H10059P | 346 | 73 | −9 | 65 | 100 | 11 |
| H1H10061P | 279 | 79 | −5 | 75 | 100 | 5 |
| H1H10041P | 298 | 88 | 3 | 83 | 97 | 5 |
| H2aM10095N | 694 | 67 | 42 | 63 | 37 | 5 |
| H1H10045P | 343 | 82 | 52 | 77 | 36 | 6 |
| H1H10031P | 405 | 60 | 45 | 57 | 25 | 6 |
| H2aM10207N | 836 | 49 | 37 | 45 | 24 | 9 |
| H1H10026P | 364 | 104 | 84 | 106 | 19 | −2 |
| H2aM10288N | 699 | 93 | 86 | 88 | 8 | 6 |
| H1H10058P | 270 | 59 | 57 | 56 | 4 | 5 |
| H2aM10293N | 532 | 93 | 91 | 90 | 2 | 3 |
| H2aM10094N | 787 | 210 | 206 | 205 | 2 | 2 |
| H2aM10289N | 819 | 209 | 205 | 205 | 2 | 2 |
| H2aM10202N | 693 | 77 | 76 | 76 | 2 | 2 |
| H2aM10208N | 743 | 176 | 188 | 176 | −7 | 0 |
| H2bM10205N | 607 | 173 | 188 | 162 | −9 | 7 |
| H2bM10203N | 557 | 159 | 177 | 156 | −11 | 2 |
| H2bM10206N | 553 | 161 | 180 | 156 | −12 | 3 |
| H2aM10291N | 601 | 186 | 210 | 188 | −13 | −1 |
| H1H10069P | 376 | 54 | 62 | 52 | −13 | 5 |
| H2aM10297N | 534 | 148 | 170 | 148 | −15 | 0 |
| H1H10067P | 332 | 85 | 98 | 82 | −16 | 4 |
| H2aM10295N | 593 | 172 | 204 | 172 | −19 | 0 |
| H1H10027P | 312 | 95 | 118 | 92 | −24 | 4 |
| H2aM10092N | 515 | 21 | 8 | 16 | IC | IC |
| H2aM10290N | 563 | 2 | 1 | 3 | IC | IC |
| H2aM10292N | 516 | 14 | 10 | 11 | IC | IC |
| H1M10096N | 454 | 22 | 18 | 19 | IC | IC |
| H2bM10097N | 677 | 1 | −2 | 0 | IC | IC |
| H2aM10294N | 657 | 6 | −1 | 4 | IC | IC |
| H2aM10296N | 728 | −4 | −5 | −5 | IC | IC |
| H1H10040P | 326 | 14 | −4 | 11 | IC | IC |

Most antibodies bound strongly to SRA; however 10 antibodies blocked the binding of apoL1 to SRA at pH 4.5.

Example 7

Octet 31×31 Cross-Competition Assay

Figure 2:
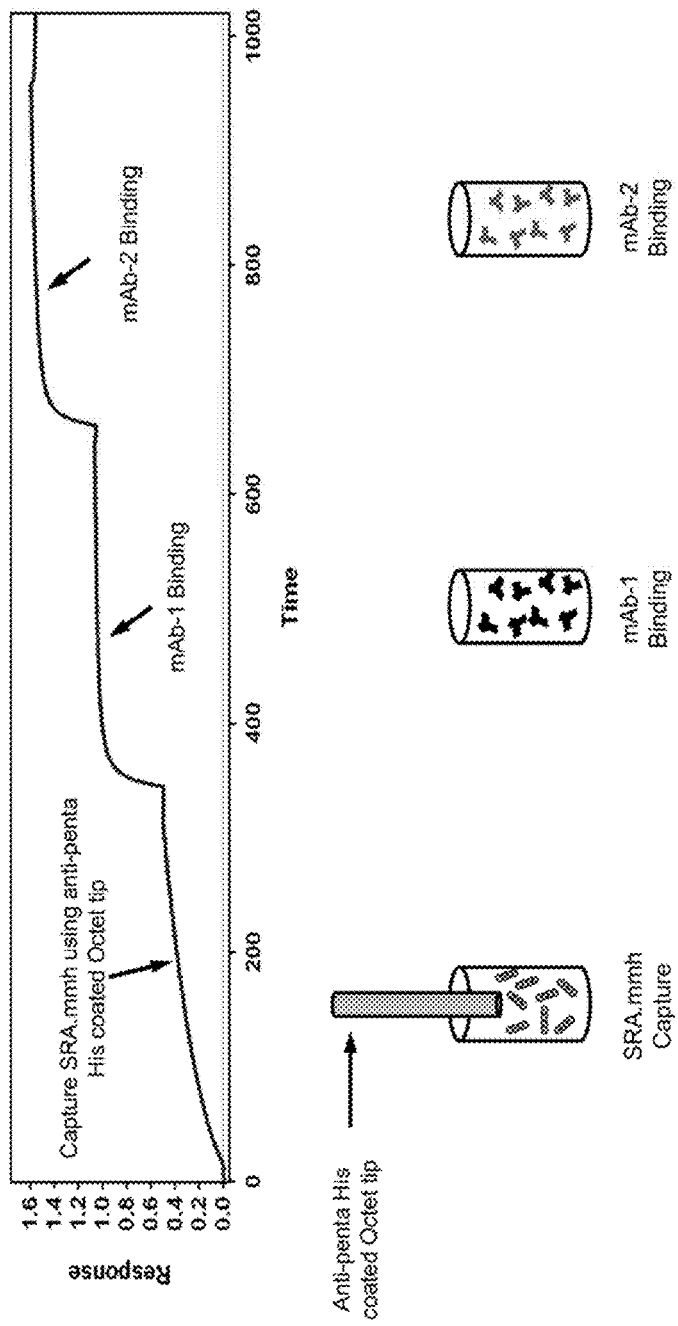
FIG. 2 shows a graph of binding response during the SRA octet cross competition assay.
Figure 3:
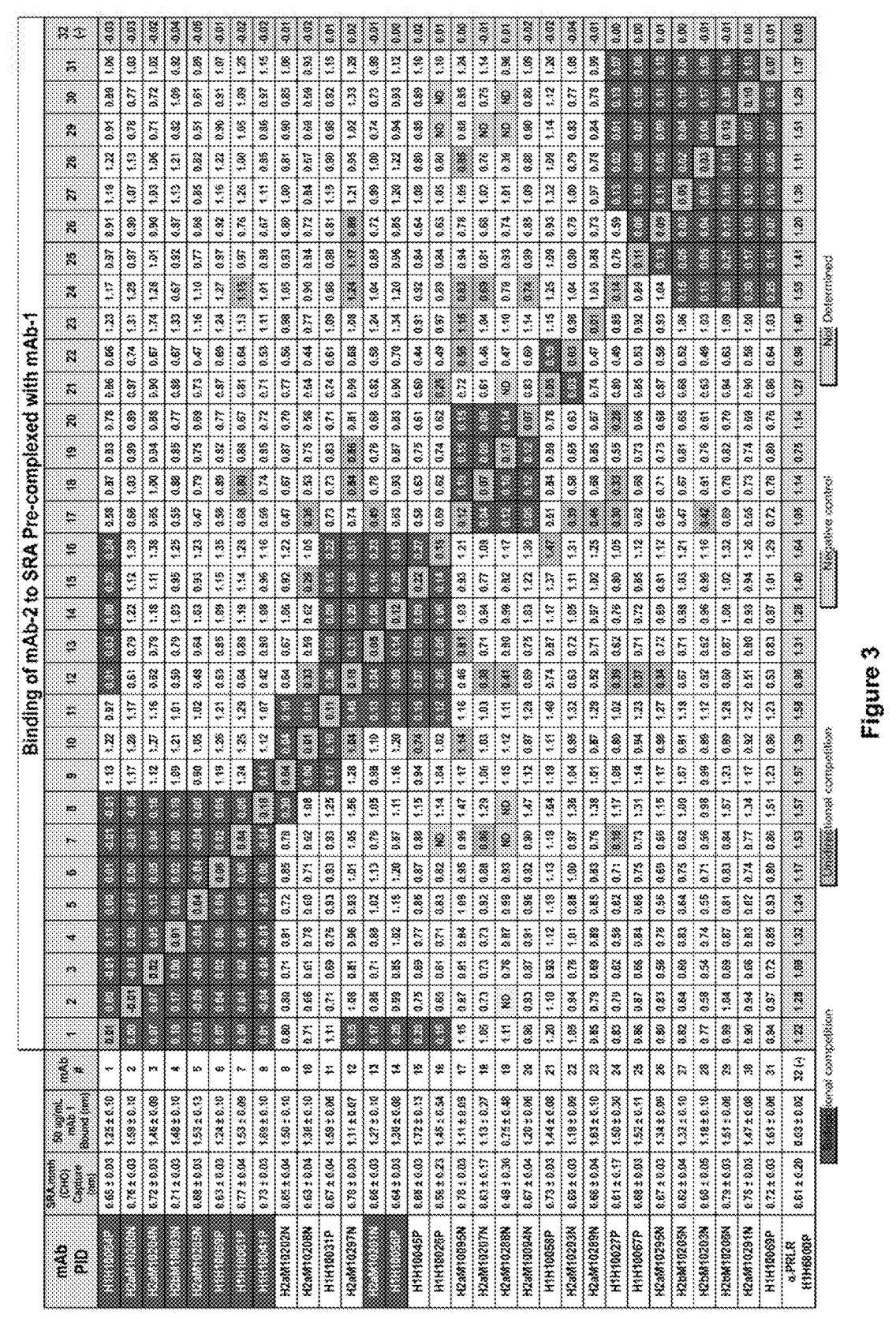

The cross-competition between anti-SRA monoclonal antibodies was performed on Octet QK384 biosensor (Fortebio Inc.). The entire experiment was performed at 25° C. with the flow rate of 1000 rpm in Octet HBST buffer (0.01M HEPES pH 7.4, 0.15M NaCl, 3 mM EDTA, 0.05% v/v Surfactant P20, 0.1 mg/ml BSA). To assess whether 2 antibodies were able to compete with one another for binding to their respective epitopes on SRA.mmh (SEQ ID NO: 291), around ~0.7 nm of SRA.mmh was first captured onto the anti-Penta-His antibody coated Octet sensor tips (Catalog#18-5079) by dipping the tips for 5 min in 20 µg/ml solution of SRA.mmh. Sensor tips captured with SRA.mmh were then dipped into wells containing 50 µg/ml solution of individual anti-SRA monoclonal antibodies (subsequently referred to as mAb-1) for 5 min to saturate the SRA.mmh surface. The sensor tips were then finally dipped into wells containing 50 µg/ml solution of different anti-SRA monoclonal antibodies (subsequently referred to as mAb-2). The sensor tips were always washed in Octet HBST buffer in between every step of the experiment. Real-time binding response was monitored during the course of the experiment and the binding response at the end of every step was recorded as shown in FIG. 2. The response of mAb-2 binding to SRA.mmh pre-complexed with mAb-1 was compared and competitive/non-competitive behavior of different anti-SRA monoclonal antibodies was determined. FIG. 3 shows the results of 31×31 cross competition experiment.

Example 8

In Vitro Trypanolysis Assay

The antibodies of the present invention can be tested for their ability to cause lysis of the trypanosome parasite in an in vitro assay known in the art. As an example, *T. brucei rhodesiense* will be plated into 24-well plates at 2×10⁶/ml in HMI-9 medium supplemented with 10% human serum (which contains ~1 ug/ml trypanolytic factor (TLF); ~0.1 ug/ml of apoL1). SRA mAbs will be added to final concentrations of 10, 1, 0.1, 0.01 and 0.001 µg/ml. After 24 hours, trypanosome cell density will be determined using an automated cell counter. Inhibition of growth or lysis is assessed after comparison with controls.

It is expected that the anti-SRA antibodies will inhibit the growth of or kill the trypanosomal parasite.

Example 9

In Vivo Mouse Protection Assay

An assay for protection by the antibodies of the invention is carried out in transgenic mice that stably express human TLF or major components of TLF, viz. apoA1, apoL1 and Hpr (see, for example, US20110030078). The mice are infected with trypanocytes and administered different dosages of antibodies of the invention intraperitoneally, as described by Thomson et al (2009) in PNAS 106: 19509-19514.

It is expected that infected mice which are administered anti-SRA antibodies of the invention will show increased survival as compared to the untreated mice.

Example 10

Generation of a Bi-specific Antibody

Various bi-specific antibodies are generated for use in practicing the methods of the invention. For example, SRA-specific antibodies are generated in a bi-specific format (a "bi-specific") in which variable regions binding to distinct domains of SRA are linked together to confer dual-domain specificity within a single binding molecule. Appropriately designed bi-specifics may enhance overall SRA inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind more than one domains and a second target, such as, but not limited to, for example, a second different anti-SRA antibody, may be prepared in a bi-specific format using techniques described herein, or other techniques known to those skilled in the art. Antibody variable regions binding to distinct regions may be linked together with variable regions that bind to relevant sites on, for example, the apoL1-binding domain of SRA, to confer dual-antigen specificity within a single binding molecule. Appropriately designed bi-specifics of this nature serve a dual function. For example, in the case of a bi-specific antibody that binds both the domains, one may be able to better neutralize both the domains concurrently, without the need for administration of a composition containing two separate antibodies. Variable regions with specificity for the apoL1-binding domain are combined with a variable region with specificity for outside the apoL1-binding domain and are paired on a structural scaffold that allows each variable region to bind to the separate antigens.

What is claimed is:

1. An isolated antibody or antigen-binding fragment thereof that binds specifically to SRA at pH7.4 and remains bound at pH4;
the antibody or antigen binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

2. An isolated antibody or antigen-binding fragment thereof that binds specifically to SRA at 25° C. and acidic pH with a dissociative half-life (t½) of less than about 4 minutes, wherein the antibody binds to SRA at 25° C. at neutral pH with a t½ of greater than about 20 minutes, as determined by surface plasmon resonance;

the antibody or antigen binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

3. An isolated antibody or antigen-binding fragment thereof that binds specifically to SRA at 25° C. and acidic pH with a dissociative half-life (t½) of less than about 100 minutes, wherein the antibody binds to SRA at 25° C. at neutral pH with a t½ of greater than about 150 minutes, as determined by surface plasmon resonance;

the antibody or antigen binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

4. An isolated antibody or antigen-binding fragment thereof that binds specifically to SRA at acidic pH and at neutral pH, wherein the dissociation rate constant (kd) for the antibody binding to SRA at 25° C. is less than about $1.7\times10^{-2}$, as determined by surface plasmon resonance;

the antibody or antigen binding fragment thereof comprising a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, and 274/282.

5. An isolated antibody or antigen-binding fragment thereof that binds specifically to SRA, wherein the antibody or antigen-binding fragment thereof binds to an epitope on SRA (SEQ ID NO: 290) comprising an amino acid selected from the group consisting of S-174, I-175, V-176, K-177, K-178, P-179, K-180, G-181, A-182, P-183, D-184, K-185, T-186, A-187, A-188, D-189, E-190, L-191, V-192, T-193 and A-194;
  wherein the antibody comprises:
  three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, and 274; and three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266 and 282.

6. An isolated antibody or antigen-binding fragment thereof that competes for specific binding to SRA with an antibody or antigen-binding fragment comprising three CDRs of a HCVR, wherein the HCVR has an amino acid sequence selected from the group consisting of SEQ ID NOs: 2, 18, 34, 50, 66, 82, 98, 114, 130, 146, 162, 178, 194, 210, 226, 242, 258, and 274; and three CDRs of a LCVR, wherein the LCVR has an amino acid sequence selected from the group consisting of SEQ ID NOs: 10, 26, 42, 58, 74, 90, 106, 122, 138, 154, 170, 186, 202, 218, 234, 250, 266, and 282.

7. The isolated antibody or antigen-binding fragment thereof of claim 6, comprising:
  (a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, and 276;
  (b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, and 278;
  (c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, and 280;
  (d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, and 284;
  (e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, and 286; and
  (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, and 288.

8. The isolated antibody or antigen-binding fragment of claim 7, wherein the antibody:
  blocks SRA binding to apoL1, wherein the antibody comprises a HCVR/LCVR amino acid sequence pair selected from the group consisting of SEQ ID NOs: 66/74, 98/106, 130/138, 146/154, 162/170, 210/218, 226/234, 242/250, 258/266, and 274/282; or
  does not block SRA binding to apoL1, wherein the antibody comprises a HCVR/LCVR amino acid sequence pair selected from the group consisting of SEQ ID NOs: 2/10, 18/26, 34/42, 50/58, 82/90, 114/122, 178/186, and 194/202.

9. An isolated antibody or antigen-binding fragment thereof that binds to SRA and blocks SRA binding to apoL1 at pH ranging from about 7.4 to about 4.5, the antibody or antigen-binding fragment thereof comprising three CDRs of a HCVR, wherein the HCVR has an amino acid sequence selected from the group consisting of SEQ ID NOs: 66, 98, 130, 146, 162, 210, 226, 242, 258, and 274; and three CDRs of a LCVR, wherein the LCVR has an amino acid sequence selected from the group consisting of SEQ ID NOs: 74, 106, 138, 154, 170, 218, 234, 250, 266, and 282.

10. An isolated antibody or antigen-binding fragment thereof that binds to SRA and blocks SRA binding to apoL1 at pH4.5, the antibody or antigen-binding fragment thereof comprising three CDRs of a HCVR, wherein the HCVR has an amino acid sequence selected from the group consisting of SEQ ID NOs: 66, 98, 130, 146, 162, 210, 226, 242, 258, and 274; and three CDRs of a LCVR, wherein the LCVR has an amino acid sequence selected from the group consisting of SEQ ID NOs: 74, 106, 138, 154, 170, 218, 234, 250, 266, and 282.

11. A pharmaceutical composition comprising an isolated human antibody or antigen-binding fragment thereof that binds to SRA according to claim 10 and a pharmaceutically acceptable carrier or diluent
  wherein the antibody or antigen-binding fragment thereof comprises the HCVR/LCVR amino acid sequence pair selected from the group consisting of SEQ ID NOs: 66/74, 98/106, 130/138, 146/154, 162/170, 210/218, 226/234, 242/250, 258/266, and 274/282.

12. A method for treating a patient suffering from sleeping sickness, or for treating at least one symptom or complication associated with sleeping sickness, or for treating a patient at risk for developing sleeping sickness, the method comprising administering to the patient a pharmaceutical composition comprising an effective amount of an antibody or an antigen-binding fragment thereof that binds to SRA according to claim 11, such that the sleeping sickness—associated condition or disease is either prevented, or lessened in severity and/or duration, or at least one symptom or complication associated with the condition or disease is prevented, or ameliorated, or that the frequency and/or duration of, or the severity of sleeping sickness is reduced.

13. An isolated monoclonal antibody or antigen-binding fragment thereof that specifically binds serum resistance-associated (SRA) protein from *Trypanosoma* spp, wherein the antibody comprises:
  three heavy chain complementarity determining region (CDRs) HCDR1, HCDR2 and HCDR3 comprising SEQ ID NOs: 68, 70 and 72; and
  three light chain CDRs (LCDR1, LCDR2, and LCDR3 comprising SEQ ID NOs: 76, 78 and 80.

14. The isolated monoclonal antibody of claim 13, which binds to an epitope on SRA SEQ ID NO. 290.

15. The isolated monoclonal antibody of claim 14, wherein the epitope to which the antibody binds comprises an amino acid selected from the group consisting of S-174, I-175, V-176, K-177, K-178, P-179, K-180, G-181, A-182, P-183, D-184, K-185, T-186, A-187, A-188, D-189, E-190, L-191, V-192, T-193 and A-194.

16. An isolated monoclonal antibody or antigen-binding fragment thereof that binds specifically to serum resistance-associated (SRA) protein from *Trypanosoma* spp, wherein the antibody comprises:
  three heavy chain complementarity determining region (CDRs) HCDR1, HCDR2 and HCDR3 comprising SEQ ID NOs: 68, 70 and 72; and three light chain CDRs (LCDR1, LCDR2, and LCDR3 comprising SEQ ID NOs: 76, 78 and 80, wherein the antibody binds to an epitope on SEQ ID NO. 290 of SRA wherein the epitope to which the antibody binds comprises an amino acid selected from the group consisting of S-174, I-175, V-176, K-177, K-178, P-179, K-180, G-181, A-182, P-183, D-184, K-185, T-186, A-187, A-188, D-189, E-190, L-191, V-192, T-193 and A-194.

17. The monoclonal antibody of claim 13, wherein the heavy chain variable region is comprised of SEQ ID NO:66.

18. The monoclonal antibody of claim 13, wherein the light chain variable region comprises SEQ ID NO:74.

19. The monoclonal antibody of claim 13, wherein the heavy chain variable region and light chain variable region are respectively defined by SEQ ID NO PAIR: 66/74.

20. The monoclonal antibody of claim 16, wherein the heavy chain variable region is comprised of SEQ ID NO:66.

21. The monoclonal antibody of claim 16, wherein the light chain variable region comprises SEQ ID NO:74.

22. The monoclonal antibody of claim 16, wherein the heavy chain variable region and light chain variable region are respectively defined by SEQ ID NO PAIR: 66/74.

* * * * *

SEQUENCE LISTING

```
<160> NUMBER OF SEQ ID NOS: 301

<210> SEQ ID NO 1
<211> LENGTH: 357
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc gtggtgcagc tgggaggtc cctgagactc      60 tcctgtgaag cctctggatt caccttcagt atctatggca tgcactgggt ccgccaggct     120
ccaggcaagg ggctggagtg ggtggcggtt atatcatatg atggaactaa tagatactat     180
gcagactccg tgaagggccg attcaccatc tccagagaca attccaagaa cacgctgtat     240
ctgcaaatga acagcctgag agctgaggac acggctgtgt attactgtgc gaaagtcaat     300
atctggaact tcctctttga ctactggggc cagggaaccc tggtcaccgt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Val Val Gln Pro Gly Arg
 1               5                  10                  15
```

```
Ser Leu Arg Leu Ser Cys Glu Ala Ser Gly Phe Thr Phe Ser Ile Tyr
         20                  25                  30

Gly Met His Trp Val Arg Gln Ala Pro Gly Lys Gly Leu Glu Trp Val
         35                  40                  45

Ala Val Ile Ser Tyr Asp Gly Thr Asn Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Asn Ile Trp Asn Phe Leu Phe Asp Tyr Trp Gly Gln Gly
             100                 105                 110

Thr Leu Val Thr Val Ser Ser
            115
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtatcta tggc                                  24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ile Tyr Gly
  1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatcatatg atggaactaa taga                                  24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Tyr Asp Gly Thr Asn Arg
  1               5

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcgaaagtca atatctggaa cttcctcttt gactac                              36

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ala Lys Val Asn Ile Trp Asn Phe Leu Phe Asp Tyr
 1               5                  10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gaaattgtgt tgacgcagtc tccaggcacc ctgtctttgt ctccagggga aagagccacc     60
ctctcctgca gggccagtca gagtgttagc ggcaactact tagcctggta ccagcagaaa    120
cctggccagg ctcccaggct cctcatctat ggtccatcca gcagggccac tggcatccca    180
gacaggttca gtggcagtgg gtctgggaca gacttcactc tcaccatcag cagactggag    240
cctgaagatt ttgcagtgta ttactgtcag cagtatggta cctcactcac tttcggcgga    300
gggaccaagg tggagatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Gly Asn
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Leu
                85                  90                  95

Thr Phe Gly Gly Gly Thr Lys Val Glu Ile Lys
            100                 105

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagagtgtta gcggcaacta c                                              21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gln Ser Val Ser Gly Asn Tyr
 1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtccatcc                                                             9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Pro Ser
 1

<210> SEQ ID NO 15
<211> LENGTH: 24
<212> TYPE: DNA
<213> ORGANISM: Artificial Sequence
<220> FEATURE:
<223> OTHER INFORMATION: Synthetic

<400> SEQUENCE: 15
cagcagtatg gtacctcact cact                                           24

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gln Gln Tyr Gly Thr Ser Leu Thr
 1               5

<210> SEQ ID NO 17
<211> LENGTH: 369
<212> TYPE: DNA
<213> ORGANISM: Artificial Sequence
<220> FEATURE:
<223> OTHER INFORMATION: Synthetic

<400> SEQUENCE: 17
gaagtgcagc tggtggagtc tgggggagcc ttggtacagc ctggcaggtc cctgacactc      60

-continued

```
tcctgtgcag cttctggctt cacctttgat gattatacca tgcactgggt ccgacaaact    120
ccagggaagg gcctggaatg ggtctcaggt attctttgga acagtgataa tttagtctat    180
gcggactctg tgaagggccg attcaccatc tccagagaca acgccaagaa ctccctgtat    240
ctgcaaatga acagtctgag agttgaggac acggccttat attattgtac aaaagagata    300
gactacctaa ccctcggggg aaatgctttt gatgtctggg gccaagggac aatggtcacc    360
gtctcttca                                                            369
```

<210> SEQ ID NO 18
<211> LENGTH: 123
<212> TYPE: PRT
<213> ORGANISM: Artificial Sequence
<220> FEATURE:
<223> OTHER INFORMATION: Synthetic

<400> SEQUENCE: 18

```
Glu Val Gln Leu Val Glu Ser Gly Gly Ala Leu Val Gln Pro Gly Arg
 1               5                  10                  15

Ser Leu Thr Leu Ser Cys Ala Ala Ser Gly Phe Thr Phe Asp Asp Tyr
            20                  25                  30

Thr Met His Trp Val Arg Gln Thr Pro Gly Lys Gly Leu Glu Trp Val
        35                  40                  45

Ser Gly Ile Leu Trp Asn Ser Asp Asn Leu Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Thr Lys Glu Ile Asp Tyr Leu Thr Leu Gly Gly Asn Ala Phe Asp Val
            100                 105                 110

Trp Gly Gln Gly Thr Met Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggcttcacct ttgatgatta tacc                                            24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Asp Asp Tyr Thr
 1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

```
<400> SEQUENCE: 21
attctttgga acagtgataa ttta                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Leu Trp Asn Ser Asp Asn Leu
 1               5

<210> SEQ ID NO 23
<211> LENGTH: 48
<212> TYPE: DNA
<213> ORGANISM: Artificial Sequence
<220> FEATURE:
<223> OTHER INFORMATION: Synthetic

<400> SEQUENCE: 23 acaaagaga tagactacct aaccctcggg ggaaatgctt ttgatgtc               48

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

Thr Lys Glu Ile Asp Tyr Leu Thr Leu Gly Gly Asn Ala Phe Asp Val
 1               5                  10                  15

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccttccacc ctgtctgcat ctgtaggaga cagaatcacc   60
atcacttgcc gggccagtca gaatattaat tactggttgg cctggtatca gcagaaacca  120
gggaaagccc ctaaactcct gatctataag gcgtctagtt tagcaggtgg ggtcccatcc  180
aggttcagcg gcagtgggtc tgggacagat ttcactctca ccatcaacag cctgcagcct  240
gatgattttg caacttatta ctgccaaaag tataatactt attcgctcaa tttcggcgga  300
gggaccaagg tggagatcaa a                                            321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Thr Leu Ser Ala Ser Val Gly
 1               5                  10                  15

Asp Arg Ile Thr Ile Thr Cys Arg Ala Ser Gln Asn Ile Asn Tyr Trp
             20                  25                  30
```

Leu Ala Trp Tyr Gln Gln Lys Pro Gly Lys Ala Pro Lys Leu Leu Ile
            35                  40                  45
Tyr Lys Ala Ser Ser Leu Ala Gly Gly Val Pro Ser Arg Phe Ser Gly
        50                  55                  60
Ser Gly Ser Gly Thr Asp Phe Thr Leu Thr Ile Asn Ser Leu Gln Pro
65                  70                  75                  80
Asp Asp Phe Ala Thr Tyr Tyr Cys Gln Lys Tyr Asn Thr Tyr Ser Leu
                85                  90                  95
Asn Phe Gly Gly Gly Thr Lys Val Glu Ile Lys
                100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagaatatta attactgg                                                18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Asn Ile Asn Tyr Trp
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 aaggcgtct                                                           9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Lys Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caaaagtata atacttattc gctcaat                                       27

```
<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Lys Tyr Asn Thr Tyr Ser Leu Asn
 1               5

<210> SEQ ID NO 33
<211> LENGTH: 351
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaaat gtggtacggc ccgggggggtc cctgagactc      60 tcctgttcag gctctggatt cgcgtttgaa aattatggaa tgagttgggt ccgccaaggt     120
ccaggaaagg gctggaatg gtctctaat attaattgga atggtggtag tttaaattat        180
gtggactctg tgaagggccg cttcaccatc tccagagaca cgccaagaa ctccctgtat      240 ctgcaaatga acagtctgag agccgaggac acggccttgt attattgtgc gagagtaatc     300
gtttacggta tggacgtctg gggccaaggg accacggtca ccgtctcctc a              351

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Asn Val Val Arg Pro Gly Gly
 1               5                  10                  15

Ser Leu Arg Leu Ser Cys Ser Gly Ser Gly Phe Ala Phe Glu Asn Tyr
             20                  25                  30

Gly Met Ser Trp Val Arg Gln Gly Pro Gly Lys Gly Leu Glu Trp Val
         35                  40                  45

Ser Asn Ile Asn Trp Asn Gly Gly Ser Leu Asn Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Val Ile Val Tyr Gly Met Asp Val Trp Gly Gln Gly Thr Thr
            100                 105                 110

Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcgcgt ttgaaaatta tgga                                              24
```

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Ala Phe Glu Asn Tyr Gly
 1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attaattgga atggtggtag ttta                                          24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Asn Trp Asn Gly Gly Ser Leu
 1               5

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
gcgagagtaa tcgtttacgg tatggacgtc                                    30

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Ala Arg Val Ile Val Tyr Gly Met Asp Val
 1               5                  10

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctcc ctgtctgcat ctgtgggaga cagagtcacc    60
atcacttgcc gggcaagtca gggcattaga aatggtttag ctggtttca gcagaaacca   120 gggaaagccc ctaaacgcct catatatgct acatccagtt tacaaagtgg ggtcccatca   180

```
aggttcagtg gcagtggatc tgggacagaa ttcactctca caatcagcag cctacagcct      240
gaggattttg cgacttatta ctgtctacag tctaatagtt acccgtggac gttcggccaa      300
gggaccaagg tggaaatcaa a                                                321
```

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Phe Gln Gln Lys Pro Gly Lys Ala Pro Lys Arg Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Ser Asn Ser Tyr Pro Trp
                85                  90                  95

Thr Phe Gly Gln Gly Thr Lys Val Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

```
cagggcatta gaaatggt                                                     18
```

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

```
Gln Gly Ile Arg Asn Gly
1               5
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

```
gctacatcc                                                               9
```

<210> SEQ ID NO 46
<211> LENGTH: 3
<212> TYPE: PRT

```
<213> ORGANISM: Artificial Sequence
<220> FEATURE:
<223> OTHER INFORMATION: Synthetic

<400> SEQUENCE: 46

Ala Thr Ser
  1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
ctacagtcta atagttaccc gtggacg                                          27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Gln Ser Asn Ser Tyr Pro Trp Thr
  1               5

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg ggctggaatg ggtggcagtt ataaggaatg atggaagtaa taaaaattat     180
gcagactccg tgaagggccg attcaccatc tccagagaca actccaagaa cactctgtat     240
ttggaaatga acagtctgag agccgaggac acggctggat attactgtgt gagagaaggg     300
gtggccggat actactttga ctactggggc cagggaaccc tggtcaccgt ctcctca       357

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Arg Asn Asp Gly Ser Asn Lys Asn Tyr Ala Asp Ser Val
         50                  55                  60

Lys Gly Arg Phe Thr Ile Ser Arg Asp Asn Ser Lys Asn Thr Leu Tyr
```

65                  70                  75                  80
Leu Glu Met Asn Ser Leu Arg Ala Glu Asp Thr Ala Gly Tyr Tyr Cys
                        85                  90                  95
Val Arg Glu Gly Val Ala Gly Tyr Tyr Phe Asp Tyr Trp Gly Gln Gly
                    100                 105                 110
Thr Leu Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagtta tggc                                            24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Gly
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
ataaggaatg atggaagtaa taaa                                            24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Arg Asn Asp Gly Ser Asn Lys
1               5

<210> SEQ ID NO 55
<211> LENGTH: 36
<212> TYPE: DNA
<213> ORGANISM: Artificial Sequence
<220> FEATURE:
<223> OTHER INFORMATION: Synthetic

<400> SEQUENCE: 55
gtgagagaag gggtggccgg atactacttt gactac                               36

<210> SEQ ID NO 56
<211> LENGTH: 12
<212> TYPE: PRT
<213> ORGANISM: Artificial Sequence
<220> FEATURE:

-continued

<223> OTHER INFORMATION: Synthetic

<400> SEQUENCE: 56

Val Arg Glu Gly Val Ala Gly Tyr Tyr Phe Asp Tyr
1               5                   10

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcttcc gtgtctgcat ctgtcggaga cagagtcacc     60
atcacttgtc gggcgagtca gggtattagc agctggttag cctggtatca gcagaaacca    120
gggagatccc ctaagctcct gatctatgct gcatccggtt tacatagtgg ggtcccatca    180
aggttcagcg gcagtggatc tgggacagat ttcactctcg ccatcagcag cctgcagcct    240
gaagatgttg caacttatta ctgtcaaaag tataacagtg ccccgctcac tttcggcgga    300
gggaccaaag tggatatcaa a                                              321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ser Pro Lys Leu Leu Ile
        35                  40                  45

Tyr Ala Ala Ser Gly Leu His Ser Gly Val Pro Ser Arg Phe Ser Gly
    50                  55                  60

Ser Gly Ser Gly Thr Asp Phe Thr Leu Ala Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Asp Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggtatta gcagctgg                                                   18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Ser Ser Trp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                                  9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caaaagtata acagtgcccc gctcact                                             27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Lys Tyr Asn Ser Ala Pro Leu Thr
 1               5

<210> SEQ ID NO 65
<211> LENGTH: 351
<212> TYPE: DNA
<213> ORGANISM: Artificial Sequence
<220> FEATURE:
<223> OTHER INFORMATION: Synthetic

<400> SEQUENCE: 65
caggtccagc tggtgcagtc tggggctgag gtgaggaagc ctgggtcctc aatgaaggtc         60
tcctgcgcga cttctggagg caactttaga agttatacta tcaactgggt gcggcaggcc        120
cctggacaag gcttgagtg gatgggagga gtcttccctg ccgttggtac aagaatctac         180
gcacagaagt tccagggcag agtcacgatt agcacggacg aatccacgac catagcctac        240
atggagctga acagtctagt acctgaggac acggccgtat attactgtgc gagatcgttt        300
aatagtcctt tgacttctg ggaccaggga accctggtca ctgtctcctc a                 351

```
<210> SEQ ID NO 66
<211> LENGTH: 117
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Ala Glu Val Arg Lys Pro Gly Ser
 1               5                  10                  15

Ser Met Lys Val Ser Cys Ala Thr Ser Gly Gly Asn Phe Arg Ser Tyr
             20                  25                  30

Thr Ile Asn Trp Val Arg Gln Ala Pro Gly Gln Gly Leu Glu Trp Met
         35                  40                  45

Gly Gly Val Phe Pro Ala Val Gly Thr Arg Ile Tyr Ala Gln Lys Phe
     50                  55                  60

Gln Gly Arg Val Thr Ile Ser Thr Asp Glu Ser Thr Ile Ala Tyr
 65                  70                  75                  80

Met Glu Leu Asn Ser Leu Val Pro Glu Asp Thr Ala Val Tyr Tyr Cys
                 85                  90                  95

Ala Arg Ser Phe Asn Ser Pro Phe Asp Phe Trp Asp Gln Gly Thr Leu
            100                 105                 110

Val Thr Val Ser Ser
        115

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggaggcaact ttagaagtta tact                                          24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Gly Asn Phe Arg Ser Tyr Thr
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
gtcttccctg ccgttggtac aaga                                          24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70
```

```
Val Phe Pro Ala Val Gly Thr Arg
  1               5
```

<210> SEQ ID NO 71
<211> LENGTH: 30
<212> TYPE: DNA
<213> ORGANISM: Artificial Sequence
<220> FEATURE:
<223> OTHER INFORMATION: Synthetic

<400> SEQUENCE: 71
gcgagatcgt ttaatagtcc ttttgacttc                                      30

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

```
Ala Arg Ser Phe Asn Ser Pro Phe Asp Phe
  1               5                  10
```

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gccatccaga tgacccagtc tccatcctcc ctgtctgcat ctgtaggaga cagagtcacc      60
ctcacttgcc gggcaagtca ggacattaga aatgatttac actggtttca gcagacacca    120
gggaaagccc cgaggctcct gatctactct gcatccaatt tacaaagtgg gtcccatca     180 aggttcagcg gcactggatc tggcacagat ttcactctca ccttcagcag cctgcagcct    240
gaagattttg caacttatta ctgtctccag gattacagtt acccgtacac ttttggccag    300
gggaccaagc tggagatcaa a                                              321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

```
Ala Ile Gln Met Thr Gln Ser Pro Ser Ser Leu Ser Ala Ser Val Gly
  1               5                  10                  15

Asp Arg Val Thr Leu Thr Cys Arg Ala Ser Gln Asp Ile Arg Asn Asp
             20                  25                  30

Leu His Trp Phe Gln Gln Thr Pro Gly Lys Ala Pro Arg Leu Leu Ile
         35                  40                  45

Tyr Ser Ala Ser Asn Leu Gln Ser Gly Val Pro Ser Arg Phe Ser Gly
     50                  55                  60

Thr Gly Ser Gly Thr Asp Phe Thr Leu Thr Phe Ser Ser Leu Gln Pro
 65                  70                  75                  80

Glu Asp Phe Ala Thr Tyr Tyr Cys Leu Gln Asp Tyr Ser Tyr Pro Tyr
                 85                  90                  95
```

Thr Phe Gly Gln Gly Thr Lys Leu Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
caggacatta gaaatgat                                                   18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Asp Ile Arg Asn Asp
 1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 tctgcatcc                                                              9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ser Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
ctccaggatt acagttaccc gtacact                                          27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Leu Gln Asp Tyr Ser Tyr Pro Tyr Thr
 1               5

<210> SEQ ID NO 81
<211> LENGTH: 357
<212> TYPE: DNA
<213> ORGANISM: Artificial Sequence
<220> FEATURE:
<223> OTHER INFORMATION: Synthetic

<400> SEQUENCE: 81

```
caggtgcagc tggtggagtc tgggggaggc gtggtccagc ctgggaggtc cctgagactc      60
tcctgtgaaa cgtctggatt caccttcagt acctatgaca tacactgggt ccgccagggt     120
ccaggcaagg ggctggagtg ggtggccagt ttacggcatg atgcgaatga taagtttct      180
gcagactccg cgaagggccg attcaccatc tccagtgaca attccaggaa tactctctat     240
ttacaaatga ccagcctgag agccgaggac acggctgtgt attattgtgt gagagaaggg     300
atagccggat actactttga ctactggggc caggggaccc tggtcaccgt ctcctca        357
```

<210> SEQ ID NO 82
<211> LENGTH: 119
<212> TYPE: PRT
<213> ORGANISM: Artificial Sequence
<220> FEATURE:
<223> OTHER INFORMATION: Synthetic

<400> SEQUENCE: 82

```
Gln Val Gln Leu Val Glu Ser Gly Gly Gly Val Val Gln Pro Gly Arg
 1               5                  10                  15

Ser Leu Arg Leu Ser Cys Glu Thr Ser Gly Phe Thr Phe Ser Thr Tyr
            20                  25                  30

Asp Ile His Trp Val Arg Gln Gly Pro Gly Lys Gly Leu Glu Trp Val
        35                  40                  45

Ala Ser Leu Arg His Asp Ala Asn Asp Lys Phe Ser Ala Asp Ser Ala
    50                  55                  60

Lys Gly Arg Phe Thr Ile Ser Ser Asp Asn Ser Arg Asn Thr Leu Tyr
65                  70                  75                  80

Leu Gln Met Thr Ser Leu Arg Ala Glu Asp Thr Ala Val Tyr Tyr Cys
                85                  90                  95

Val Arg Glu Gly Ile Ala Gly Tyr Tyr Phe Asp Tyr Trp Gly Gln Gly
           100                 105                 110

Thr Leu Val Thr Val Ser Ser
       115
```

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83

```
ggattcacct tcagtaccta tgac                                             24
```

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

```
Gly Phe Thr Phe Ser Thr Tyr Asp
 1               5
```

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
ttacggcatg atgcgaatga taag                                         24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Leu Arg His Asp Ala Asn Asp Lys
 1               5

<210> SEQ ID NO 87
<211> LENGTH: 36
<212> TYPE: DNA
<213> ORGANISM: Artificial Sequence
<220> FEATURE:
<223> OTHER INFORMATION: Synthetic

<400> SEQUENCE: 87
gtgagagaag ggatagccgg atactacttt gactac                            36

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Val Arg Glu Gly Ile Ala Gly Tyr Tyr Phe Asp Tyr
 1               5                  10

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatctttc gtgtctgcat ctgtaggaga cagagtcacc    60
atctcttgtc gggcgagtca ggatattcac acctggttag cctggtatca gcagaaacca   120
gggaaagccc ctaacctcct gatctatgct gcatccggtt tacatagtag ggccccatca   180
agattcagcg gcagtggttc tgggacagat ttcactctca ccatcagcag cctgcagcct   240
gaagattttg caacttacta ttgtcaaaag gctgacagat tcccattcac tttcggccct   300
gggaccaaag tggatatcaa a                                            321

<210> SEQ ID NO 90
<211> LENGTH: 107
<212> TYPE: PRT
<213> ORGANISM: Artificial Sequence
<220> FEATURE:

<223> OTHER INFORMATION: Synthetic

<400> SEQUENCE: 90

Asp Ile Gln Met Thr Gln Ser Pro Ser Phe Val Ala Ser Val Gly
1               5                   10                  15

Asp Arg Val Thr Ile Ser Cys Arg Ala Ser Gln Asp Ile His Thr Trp
            20                  25                  30

Leu Ala Trp Tyr Gln Gln Lys Pro Gly Lys Ala Pro Asn Leu Leu Ile
        35                  40                  45

Tyr Ala Ala Ser Gly Leu His Ser Arg Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Asp Arg Phe Pro Phe
                85                  90                  95

Thr Phe Gly Pro Gly Thr Lys Val Asp Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
caggatattc acacctgg                                                     18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Asp Ile His Thr Trp
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                                9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA

<213> ORGANISM: Artificial Sequence
<220> FEATURE:
<223> OTHER INFORMATION: Synthetic

<400> SEQUENCE: 95
caaaaggctg acagattccc attcact        27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Lys Ala Asp Arg Phe Pro Phe Thr
1               5

<210> SEQ ID NO 97
<211> LENGTH: 357
<212> TYPE: DNA
<213> ORGANISM: Artificial Sequence
<220> FEATURE:
<223> OTHER INFORMATION: Synthetic

<400> SEQUENCE: 97
caggtgcagc tggtggagtc tgggggaggc gtggtccagc ctggagggtc cctgagactc        60
tcctgttcag cctctggatt caccttcagt ctctatggca tgcactggat ccgccaggct       120
ccaggcaagg ggctggagtg ggtggcagtt atttcatatg atggaagtaa tacatattat       180
ggagactccg tgaagggccg attcaccatc tccagagaca attccaagaa cacgctgtat       240
ctgcaaatga acagcctgag aactgaggac acggctattt attactgtgc gaaagtgtat       300
aactggaact accttttttga ctactggggc cagggaaccc tggtcaccgt ctcctca        357

<210> SEQ ID NO 98
<211> LENGTH: 119
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Glu Ser Gly Gly Gly Val Val Gln Pro Gly Arg
1               5                   10                  15
Ser Leu Arg Leu Ser Cys Ser Ala Ser Gly Phe Thr Phe Ser Leu Tyr
            20                  25                  30
Gly Met His Trp Ile Arg Gln Ala Pro Gly Lys Gly Leu Glu Trp Val
        35                  40                  45
Ala Val Ile Ser Tyr Asp Gly Ser Asn Thr Tyr Tyr Gly Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Thr Glu Asp Thr Ala Ile Tyr Tyr Cys
                85                  90                  95
Ala Lys Val Tyr Asn Trp Asn Tyr Leu Phe Asp Tyr Trp Gly Gln Gly
            100                 105                 110
Thr Leu Val Thr Val Ser Ser
        115

<210> SEQ ID NO 99

```
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct tcagtctcta tggc                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Leu Tyr Gly
 1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
atttcatatg atggaagtaa taca                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Tyr Asp Gly Ser Asn Thr
 1               5

<210> SEQ ID NO 103
<211> LENGTH: 36
<212> TYPE: DNA
<213> ORGANISM: Artificial Sequence
<220> FEATURE:
<223> OTHER INFORMATION: Synthetic

<400> SEQUENCE: 103
gcgaaagtgt ataactggaa ctaccttttt gactac                             36

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

Ala Lys Val Tyr Asn Trp Asn Tyr Leu Phe Asp Tyr
 1               5                  10

<210> SEQ ID NO 105
<211> LENGTH: 321
<212> TYPE: DNA
<213> ORGANISM: Artificial Sequence
<220> FEATURE:
```

<223> OTHER INFORMATION: Synthetic

<400> SEQUENCE: 105

```
gaaattgtgt tgacgcagtc tccagacacc ctgtctttgt ctccagggga aagagccacc      60
ctctcctgca gggccagtca gaatgttaac aacaacttct tagcctggta ccagcagaaa     120
cctggccagg ctcccaggct cctcatctat ggtgcatcca gcagggccac tgacatccca     180
gagaggttca gtggcagtgg gtctgggaca gacttcactc tcaccatcag cagactggag     240
cctgaagatt ttgcagtata ttattgtctg cattacgtta actcacggac gttcggccaa     300
gggaccaagg tggaaatcaa a                                               321
```

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

```
Glu Ile Val Leu Thr Gln Ser Pro Asp Thr Leu Ser Leu Ser Pro Gly
1               5                   10                  15
Glu Arg Ala Thr Leu Ser Cys Arg Ala Ser Gln Asn Val Asn Asn Asn
            20                  25                  30
Phe Leu Ala Trp Tyr Gln Gln Lys Pro Gly Gln Ala Pro Arg Leu Leu
        35                  40                  45
Ile Tyr Gly Ala Ser Ser Arg Ala Thr Asp Ile Pro Glu Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Leu His Tyr Val Asn Ser Arg
                85                  90                  95
Thr Phe Gly Gln Gly Thr Lys Val Glu Ile Lys
            100                 105
```

<210> SEQ ID NO 107
<211> LENGTH: 21
<212> TYPE: DNA
<213> ORGANISM: Artificial Sequence
<220> FEATURE:
<223> OTHER INFORMATION: Synthetic

<400> SEQUENCE: 107

```
cagaatgtta acaacaactt c                                                21
```

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

```
Gln Asn Val Asn Asn Asn Phe
1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 ggtgcatcc                                                                9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Gly Ala Ser
 1

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
ctgcattacg ttaactcacg gacg                                              24

<210> SEQ ID NO 112
<211> LENGTH: 8
<212> TYPE: PRT
<213> ORGANISM: Artificial Sequence
<220> FEATURE:
<223> OTHER INFORMATION: Synthetic

<400> SEQUENCE: 112

Leu His Tyr Val Asn Ser Arg Thr
 1               5

<210> SEQ ID NO 113
<211> LENGTH: 342
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtccagc cggggggtc cctgagactc        60 tcctgtgcag cctcagggtt cacatttaat gattttttta tgagttgggt ccgccaggct      120
ccagggaagg ggctggagtg ggtggccaat ttaaaccaag atggaagtga gagacactat      180
gtggactctg tgaagggccg attcaccatc tccagagaca acgccaagaa ttcactgtct      240
ctgcaaatga atagcctgag agtcgaggac acggctgtat attactgtgc gcagaggggg      300
ggggactcct ggggccaggg aaccctggtc accgtctcct ca                         342

<210> SEQ ID NO 114
<211> LENGTH: 114
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Asp Phe

```
                20                  25                  30
Phe Met Ser Trp Val Arg Gln Ala Pro Gly Lys Gly Leu Glu Trp Val
            35                  40                  45
Ala Asn Leu Asn Gln Asp Gly Ser Glu Arg His Tyr Val Asp Ser Val
        50                  55                  60
Lys Gly Arg Phe Thr Ile Ser Arg Asp Asn Ala Lys Asn Ser Leu Ser
65                  70                  75                  80
Leu Gln Met Asn Ser Leu Arg Val Glu Asp Thr Ala Val Tyr Tyr Cys
                85                  90                  95
Ala Arg Glu Gly Gly Asp Ser Trp Gly Gln Gly Thr Leu Val Thr Val
                100                 105                 110
Ser Ser

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
gggttcacat ttaatgattt tttt                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Asn Asp Phe Phe
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
ttaaaccaag atggaagtga gaga                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Leu Asn Gln Asp Gly Ser Glu Arg
1               5

<210> SEQ ID NO 119
<211> LENGTH: 21
<212> TYPE: DNA
<213> ORGANISM: Artificial Sequence
<220> FEATURE:
<223> OTHER INFORMATION: Synthetic

<400> SEQUENCE: 119
```

```
gcgcgagagg gggggactc c                                                    21
```

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Ala Arg Glu Gly Gly Asp Ser
 1               5

<210> SEQ ID NO 121
<211> LENGTH: 339
<212> TYPE: DNA
<213> ORGANISM: Artificial Sequence
<220> FEATURE:
<223> OTHER INFORMATION: Synthetic

<400> SEQUENCE: 121

```
gacatcgtga tgacccagtc tccagactcc ctggctgtgt ctctgggcga gagggtcacc    60
atcaactgca agtccagcca gagtatttta tacagtgcca acaataagga ctacttagct   120
tggtttcacc agaaaccagg acagcctcct aaactgctca tttactgggc atctatccgg   180
gaatccgggg tccctgaccg aatcagtggc agcgggtctg ggacagactt cactctcacc   240
atcagcagcc tgcaggctga agatgtggct gtttattact gtcagcaata ttatcttttt   300
cctccgacgt tcggccaagg gaccaaggtg gaaatcaaa                           339
```

<210> SEQ ID NO 122
<211> LENGTH: 113
<212> TYPE: PRT
<213> ORGANISM: Artificial Sequence
<220> FEATURE:
<223> OTHER INFORMATION: Synthetic

<400> SEQUENCE: 122

Asp Ile Val Met Thr Gln Ser Pro Asp Ser Leu Ala Val Ser Leu Gly
 1               5                  10                  15

Glu Arg Val Thr Ile Asn Cys Lys Ser Ser Gln Ser Ile Leu Tyr Ser
                20                  25                  30

Ala Asn Asn Lys Asp Tyr Leu Ala Trp Phe His Gln Lys Pro Gly Gln
            35                  40                  45

Pro Pro Lys Leu Leu Ile Tyr Trp Ala Ser Ile Arg Glu Ser Gly Val
        50                  55                  60

Pro Asp Arg Ile Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Gln
                85                  90                  95

Tyr Tyr Leu Phe Pro Pro Thr Phe Gly Gln Gly Thr Lys Val Glu Ile
            100                 105                 110

Lys

<210> SEQ ID NO 123
<211> LENGTH: 36
<212> TYPE: DNA
<213> ORGANISM: Artificial Sequence
<220> FEATURE:
<223> OTHER INFORMATION: Synthetic

<400> SEQUENCE: 123

```
cagagtattt tatacagtgc caacaataag gactac                              36
```

<210> SEQ ID NO 124
<211> LENGTH: 12
<212> TYPE: PRT
<213> ORGANISM: Artificial Sequence
<220> FEATURE:
<223> OTHER INFORMATION: Synthetic

<400> SEQUENCE: 124

```
Gln Ser Ile Leu Tyr Ser Ala Asn Asn Lys Asp Tyr
 1               5                  10
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125

```
tgggcatct                                                            9
```

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

```
Trp Ala Ser
 1
```

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127

```
cagcaatatt atcttttcc tccgacg                                         27
```

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

```
Gln Gln Tyr Tyr Leu Phe Pro Pro Thr
 1               5
```

<210> SEQ ID NO 129
<211> LENGTH: 357
<212> TYPE: DNA
<213> ORGANISM: Artificial Sequence
<220> FEATURE:
<223> OTHER INFORMATION: Synthetic

<400> SEQUENCE: 129

```
caggtgcagc tggtgcagtc tggggctgag gtgaagaagc ctggggcctc agtgaaggtc    60
tcctgcaagg ctgctggatt caccttcatc ggctattata tacactgggt gcgacaggcc   120
```

```
cctggacaag ggcttgagtg gatgggatgg atcaattcta atagtggtga caaagactct    180
gcaccgaagt ttcaggacag ggtcaccatg accagggaca cgtccatcag cacagcctac    240
atggagctga gcaggctgag atctgacgac acggccgtgt atttctgtgc gagagaggga    300
tacaactttg gtcactttga ctactggggc cagggaaccc tggtcaccgt ctcctca       357
```

<210> SEQ ID NO 130
<211> LENGTH: 119
<212> TYPE: PRT
<213> ORGANISM: Artificial Sequence
<220> FEATURE:
<223> OTHER INFORMATION: Synthetic

<400> SEQUENCE: 130

```
Gln Val Gln Leu Val Gln Ser Gly Ala Glu Val Lys Lys Pro Gly Ala
 1               5                  10                  15

Ser Val Lys Val Ser Cys Lys Ala Ala Gly Phe Thr Phe Ile Gly Tyr
            20                  25                  30

Tyr Ile His Trp Val Arg Gln Ala Pro Gly Gln Gly Leu Glu Trp Met
        35                  40                  45

Gly Trp Ile Asn Ser Asn Ser Gly Asp Lys Asp Ser Ala Pro Lys Phe
    50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Glu Gly Tyr Asn Phe Gly His Phe Asp Tyr Trp Gly Gln Gly
            100                 105                 110

Thr Leu Val Thr Val Ser Ser
        115
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

```
ggattcacct tcatcggcta ttat                                            24
```

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Phe Thr Phe Ile Gly Tyr Tyr
 1               5
```

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133

```
atcaattcta atagtggtga caaa                                            24
```

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Asn Ser Asn Ser Gly Asp Lys
 1               5

<210> SEQ ID NO 135
<211> LENGTH: 36
<212> TYPE: DNA
<213> ORGANISM: Artificial Sequence
<220> FEATURE:
<223> OTHER INFORMATION: Synthetic

<400> SEQUENCE: 135
gcgagagagg gatacaactt tggtcacttt gactac                36

<210> SEQ ID NO 136
<211> LENGTH: 12
<212> TYPE: PRT
<213> ORGANISM: Artificial Sequence
<220> FEATURE:
<223> OTHER INFORMATION: Synthetic

<400> SEQUENCE: 136

Ala Arg Glu Gly Tyr Asn Phe Gly His Phe Asp Tyr
 1               5                  10

<210> SEQ ID NO 137
<211> LENGTH: 336
<212> TYPE: DNA
<213> ORGANISM: Artificial Sequence
<220> FEATURE:
<223> OTHER INFORMATION: Synthetic

<400> SEQUENCE: 137
gatattgtga tgacccagac tccactctcc tcacctgtca cccttggaca gccggcctcc    60
atctcctgca ggtctagtca gagcctcgta cacagtgatg gaaacaccta cttgagttgg   120
cttcagcaga ggccaggcca gcctccaaga ctcctaattt ataagatttc taaccggttg   180
tctggggtcc cagacagatt cagtggcagt ggggcaggaa cagacttcac actgaaaatc   240
agcagggtgg aaggtgagga tgtcggggtt tattactgca tgcaaggtac acaatttcct   300
cggacgttcg gccaagggac caaggtggaa atcaaa                            336

<210> SEQ ID NO 138
<211> LENGTH: 112
<212> TYPE: PRT
<213> ORGANISM: Artificial Sequence
<220> FEATURE:
<223> OTHER INFORMATION: Synthetic

<400> SEQUENCE: 138

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

```
Pro Arg Leu Ile Tyr Lys Ile Ser Asn Arg Leu Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Gly Glu Asp Val Gly Val Tyr Tyr Cys Met Gln Gly
                85                  90                  95

Thr Gln Phe Pro Arg Thr Phe Gly Gln Gly Thr Lys Val Glu Ile Lys
            100                 105                 110
```

<210> SEQ ID NO 139
<211> LENGTH: 33
<212> TYPE: DNA
<213> ORGANISM: Artificial Sequence
<220> FEATURE:
<223> OTHER INFORMATION: Synthetic

<400> SEQUENCE: 139
cagagcctcg tacacagtga tggaaacacc tac        33

<210> SEQ ID NO 140
<211> LENGTH: 11
<212> TYPE: PRT
<213> ORGANISM: Artificial Sequence
<220> FEATURE:
<223> OTHER INFORMATION: Synthetic

<400> SEQUENCE: 140

```
Gln Ser Leu Val His Ser Asp Gly Asn Thr Tyr
 1               5                  10
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 aagatttct        9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

```
Lys Ile Ser
 1
```

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
atgcaaggta cacaatttcc tcggacg        27

<210> SEQ ID NO 144
<211> LENGTH: 9
<212> TYPE: PRT

```
<213> ORGANISM: Artificial Sequence
<220> FEATURE:
<223> OTHER INFORMATION: Synthetic

<400> SEQUENCE: 144

Met Gln Gly Thr Gln Phe Pro Arg Thr
 1               5

<210> SEQ ID NO 145
<211> LENGTH: 372
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggaggc gtggtccagc cagggaactc cctgagactc      60
tcctgtgcag cctctggatt caccttcagt gcctatggca tgcactgggt ccgccaggct     120
ccaggcaagg ggctggagtg gtggcagtc atatcatatg atggaagtaa tgaattctat     180
gcagactccg tgaagggccg attcaccatc ttcagagaca attccaagaa catgctgtat     240
ctacaaatga acagcctgag agttgaagac acgtctattt attactgtgc gaaagataga     300
ggactgggag tttactattt cttctacggt atggacgtct ggggccaagg gaccacggtc     360
accgtctcct ca                                                         372

<210> SEQ ID NO 146
<211> LENGTH: 124
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ala Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Glu Phe Tyr Ala Asp Ser Val
        50                  55                  60

Lys Gly Arg Phe Thr Ile Phe Arg Asp Asn Ser Lys Asn Met Leu Tyr
65                  70                  75                  80

Leu Gln Met Asn Ser Leu Arg Val Glu Asp Thr Ser Ile Tyr Tyr Cys
                85                  90                  95

Ala Lys Asp Arg Gly Leu Gly Val Tyr Tyr Phe Phe Tyr Gly Met Asp
            100                 105                 110

Val Trp Gly Gln Gly Thr Thr Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtgccta tggc                                             24
```

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Ala Tyr Gly
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atatcatatg atggaagtaa tgaa                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Tyr Asp Gly Ser Asn Glu
1               5

<210> SEQ ID NO 151
<211> LENGTH: 51
<212> TYPE: DNA
<213> ORGANISM: Artificial Sequence
<220> FEATURE:
<223> OTHER INFORMATION: Synthetic

<400> SEQUENCE: 151
gcgaaagata gaggactggg agtttactat ttcttctacg gtatggacgt c           51

<210> SEQ ID NO 152
<211> LENGTH: 17
<212> TYPE: PRT
<213> ORGANISM: Artificial Sequence
<220> FEATURE:
<223> OTHER INFORMATION: Synthetic

<400> SEQUENCE: 152

Ala Lys Asp Arg Gly Leu Gly Val Tyr Tyr Phe Phe Tyr Gly Met Asp
1               5                   10                  15

Val

<210> SEQ ID NO 153
<211> LENGTH: 339
<212> TYPE: DNA
<213> ORGANISM: Artificial Sequence
<220> FEATURE:
<223> OTHER INFORMATION: Synthetic

<400> SEQUENCE: 153
gacatcgtga tgacccagtc tccagactcc ctggttgtgt ctctgggcga gagggccacc    60
atcaactgca agtccagcca gagtctttta tacagctcca gcaataacaa ttacttaact   120

```
tggtaccagc agaaaccagg acggcctcct aagctgctca tttactgggc atctacccgg      180
gaatccgggg tccctgaccg attcagtggc agcgggtctg ggacagattt cactctcacc      240
atcagcagcc tgcaggctga ggatgtggca atttattact gtcagcaaaa ttatattact      300
ccgctcactt tcggcggagg gaccaaggtg gagatcaaa                              339
```

<210> SEQ ID NO 154
<211> LENGTH: 113
<212> TYPE: PRT
<213> ORGANISM: Artificial Sequence
<220> FEATURE:
<223> OTHER INFORMATION: Synthetic

<400> SEQUENCE: 154

```
Asp Ile Val Met Thr Gln Ser Pro Asp Ser Leu Val Val Ser Leu Gly
 1               5                  10                  15

Glu Arg Ala Thr Ile Asn Cys Lys Ser Gln Ser Leu Leu Tyr Ser
             20                  25                  30

Ser Ser Asn Asn Asn Tyr Leu Thr Trp Tyr Gln Lys Pro Gly Arg
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Ile Tyr Tyr Cys Gln Gln
                 85                  90                  95

Asn Tyr Ile Thr Pro Leu Thr Phe Gly Gly Gly Thr Lys Val Glu Ile
            100                 105                 110

Lys
```

<210> SEQ ID NO 155
<211> LENGTH: 36
<212> TYPE: DNA
<213> ORGANISM: Artificial Sequence
<220> FEATURE:
<223> OTHER INFORMATION: Synthetic

<400> SEQUENCE: 155

```
cagagtcttt tatacagctc cagcaataac aattac                                 36
```

<210> SEQ ID NO 156
<211> LENGTH: 12
<212> TYPE: PRT
<213> ORGANISM: Artificial Sequence
<220> FEATURE:
<223> OTHER INFORMATION: Synthetic

<400> SEQUENCE: 156

```
Gln Ser Leu Leu Tyr Ser Ser Ser Asn Asn Asn Tyr
 1               5                  10
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

```
tgggcatct                                                                9
```

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Trp Ala Ser
 1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
cagcaaaatt atattactcc gctcact                                         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Asn Tyr Ile Thr Pro Leu Thr
 1               5

<210> SEQ ID NO 161
<211> LENGTH: 378
<212> TYPE: DNA
<213> ORGANISM: Artificial Sequence
<220> FEATURE:
<223> OTHER INFORMATION: Synthetic

<400> SEQUENCE: 161
caggtccagc tggtgcagtc tggggctgag gtgaagaagc ctgggtcctc ggtgaaggtc      60
tcctgcaagg cttctggagg ctccttcagc agcaatgttt tcagctgggt gcgacaggcc     120
cctggacaag gcttgagtg gatgggaggg atcatcccta tctttggttc agcaaactac      180
gcacagaagt tccagggcag agtcacgatc accacggacg aatccacgac acagcctac      240 atggagctga gcagcctgag atctgaggac acggccgttt attactgtgc gataggggga     300
actggaccca gtggctataa ctggaactac ggggcttttt atatctgggg ccaagggaca     360
atggtcaccg tctcttca                                                   378

<210> SEQ ID NO 162
<211> LENGTH: 126
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ser Phe Ser Ser Asn
                20                  25                  30

Val Phe Ser Trp Val Arg Gln Ala Pro Gly Gln Gly Leu Glu Trp Met
            35                  40                  45

```
Gly Gly Ile Ile Pro Ile Phe Gly Ser Ala Asn Tyr Ala Gln Lys Phe
            50                  55                  60

Gln Gly Arg Val Thr Ile Thr Thr Asp Glu Ser Thr Thr Thr Ala Tyr
 65                  70                  75                  80

Met Glu Leu Ser Ser Leu Arg Ser Glu Asp Thr Ala Val Tyr Tyr Cys
                85                  90                  95

Ala Ile Gly Gly Thr Gly Pro Ser Gly Tyr Asn Trp Asn Tyr Gly Ala
            100                 105                 110

Phe Tyr Ile Trp Gly Gln Gly Thr Met Val Thr Val Ser Ser
            115                 120                 125
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggaggctcct tcagcagcaa tgtt         24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

```
Gly Gly Ser Phe Ser Ser Asn Val
 1               5
```

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atcatcccta tctttggttc agca         24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

```
Ile Ile Pro Ile Phe Gly Ser Ala
 1               5
```

<210> SEQ ID NO 167
<211> LENGTH: 57
<212> TYPE: DNA
<213> ORGANISM: Artificial Sequence
<220> FEATURE:
<223> OTHER INFORMATION: Synthetic

<400> SEQUENCE: 167 gcgataggggg gaactggacc cagtggctat aactggaact acggggcttt ttatatc         57

<210> SEQ ID NO 168
<211> LENGTH: 19
<212> TYPE: PRT
<213> ORGANISM: Artificial Sequence
<220> FEATURE:
<223> OTHER INFORMATION: Synthetic

<400> SEQUENCE: 168

Ala Ile Gly Gly Thr Gly Pro Ser Gly Tyr Asn Trp Asn Tyr Gly Ala
 1               5                  10                  15

Phe Tyr Ile

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggatagccc ctaagcgcct gatctatgct gcatccagtt tgcaaagtgg ggtcccatca    180
agattcagcg gcagtggatc tgggacagaa ttcactctca caatcagcag cctgcagcct    240
gaagattttg caacttatta ctgtctacaa cataatagtt acccgtacac ttttggccag    300
gggaccaagc tggagatcaa a                                              321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Ile Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagggcatta gaaatgat                                                   18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Arg Asn Asp
 1               5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatcc                                                                  9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
ctacaacata atagttaccc gtacact                                             27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Leu Gln His Asn Ser Tyr Pro Tyr Thr
 1               5

<210> SEQ ID NO 177
<211> LENGTH: 366
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtaaagc cttcacagac cctgtccctc      60
acctgcattg tctctggtgg ctccatcagc agtggtgatt attattggaa ctggatccgg     120
cagcacccag ggaagggcct ggagtggatt ggggacatct atcacagtgg ggacacctac     180

```
tacaacccgt ccctcaagag tcgcgttacc atatcacttg acacgtctaa gaaccaattc    240
tccctgaagc tgagctctct gactgccgcg gacacggccg tttattactg tgcgagagat    300
cgtatagtag caactggggg cggtatggac gtctggggcc aagggaccac ggtcaccgtc    360
tcctca                                                               366
```

<210> SEQ ID NO 178
<211> LENGTH: 122
<212> TYPE: PRT
<213> ORGANISM: Artificial Sequence
<220> FEATURE:
<223> OTHER INFORMATION: Synthetic

<400> SEQUENCE: 178

```
Gln Val Gln Leu Gln Glu Ser Gly Pro Gly Leu Val Lys Pro Ser Gln
 1               5                  10                  15

Thr Leu Ser Leu Thr Cys Ile Val Ser Gly Ser Ile Ser Ser Gly
            20                  25                  30

Asp Tyr Tyr Trp Asn Trp Ile Arg Gln His Pro Gly Lys Gly Leu Glu
         35                  40                  45

Trp Ile Gly Asp Ile Tyr His Ser Gly Asp Thr Tyr Tyr Asn Pro Ser
 50                  55                  60

Leu Lys Ser Arg Val Thr Ile Ser Leu Asp Thr Ser Lys Asn Gln Phe
 65                  70                  75                  80

Ser Leu Lys Leu Ser Ser Leu Thr Ala Ala Asp Thr Ala Val Tyr Tyr
                 85                  90                  95

Cys Ala Arg Asp Arg Ile Val Ala Thr Gly Gly Gly Met Asp Val Trp
            100                 105                 110

Gly Gln Gly Thr Thr Val Thr Val Ser Ser
        115                 120
```

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179

```
ggtggctcca tcagcagtgg tgattattat                                      30
```

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

```
Gly Gly Ser Ile Ser Ser Gly Asp Tyr Tyr
 1               5                  10
```

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181

```
atctatcaca gtggggacac c                                               21
```

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Ile Tyr His Ser Gly Asp Thr
1               5

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
gcgagagatc gtatagtagc aactgggggc ggtatggacg tc                          42

<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184

Ala Arg Asp Arg Ile Val Ala Thr Gly Gly Gly Met Asp Val
1               5                   10

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccttccacc ctgtctgcat ctgtaggaga cagagtcacc        60
atcacttgcc gggccagtca gagtattagt agttggttgg cctggtatca gcggaaacca       120
gggaaagccc ctaacctcct gatctatagg tcgtctagtt tagaaagtgg ggtcccatca       180
aggttcagcg gcagtggctc tgggacagaa ttcactctca ccatcagcag cctgcaggct       240
gatgattttg taatttatta ctgccaacag tataatagtt atccgtacac ttttggccag       300
gggaccaagc tggagatcaa a                                                 321

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Arg Lys Pro Gly Lys Ala Pro Asn Leu Leu Ile
        35                  40                  45

Tyr Arg Ser Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Ala
65                  70                  75                  80

Asp Asp Phe Val Ile Tyr Tyr Cys Gln Gln Tyr Asn Ser Tyr Pro Tyr
                85                  90                  95

Thr Phe Gly Gln Gly Thr Lys Leu Glu Ile Lys
            100                 105

```
<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagagtatta gtagttgg                                                 18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188
```

Gln Ser Ile Ser Ser Trp
 1               5

```
<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 aggtcgtct                                                            9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190
```

Arg Ser Ser
 1

```
<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacagtata atagttatcc gtacact                                       27

<210> SEQ ID NO 192
<211> LENGTH: 9
<212> TYPE: PRT
<213> ORGANISM: Artificial Sequence
```

<220> FEATURE:
<223> OTHER INFORMATION: Synthetic

<400> SEQUENCE: 192

Gln Gln Tyr Asn Ser Tyr Pro Tyr Thr
1               5

<210> SEQ ID NO 193
<211> LENGTH: 351
<212> TYPE: DNA
<213> ORGANISM: Artificial Sequence
<220> FEATURE:
<223> OTHER INFORMATION: Synthetic

<400> SEQUENCE: 193

```
caggtgcagc tgcaggagtc gggcccagga ctggtgaagc cttcggagac cctgtccctc      60
acctgctctg tctctggtgg ctccttcact aattactact ggagctggat ccggcagccc     120
cccgggaagg gactggagtg gattgggtct gtcttttaca gtgggaccac caactacaac     180
ccctccctcc agagtcgagt caccttatca atagaaacgt ccaagaacca gttctccctg     240
aggctgaact ctgtgaccgc tgcggacacg gccgtatatt actgtgctag agatcaagga     300
gcagcagcac tggactactg gggccaggga accctggtca ctgtctcctc a              351
```

<210> SEQ ID NO 194
<211> LENGTH: 117
<212> TYPE: PRT
<213> ORGANISM: Artificial Sequence
<220> FEATURE:
<223> OTHER INFORMATION: Synthetic

<400> SEQUENCE: 194

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Phe Thr Asn Tyr
            20                  25                  30

Tyr Trp Ser Trp Ile Arg Gln Pro Pro Gly Lys Gly Leu Glu Trp Ile
        35                  40                  45

Gly Ser Val Phe Tyr Ser Gly Thr Thr Asn Tyr Asn Pro Ser Leu Gln
    50                  55                  60

Ser Arg Val Thr Leu Ser Ile Glu Thr Ser Lys Asn Gln Phe Ser Leu
65                  70                  75                  80

Arg Leu Asn Ser Val Thr Ala Ala Asp Thr Ala Val Tyr Tyr Cys Ala
                85                  90                  95

Arg Asp Gln Gly Ala Ala Ala Leu Asp Tyr Trp Gly Gln Gly Thr Leu
            100                 105                 110

Val Thr Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggtggctcct tcactaatta ctac                                              24
```

<210> SEQ ID NO 196
<211> LENGTH: 8

<212> TYPE: PRT
<213> ORGANISM: Artificial Sequence
<220> FEATURE:
<223> OTHER INFORMATION: Synthetic

<400> SEQUENCE: 196

Gly Gly Ser Phe Thr Asn Tyr Tyr
 1               5

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197
gtcttttaca gtgggaccac c                                          21

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Val Phe Tyr Ser Gly Thr Thr
 1               5

<210> SEQ ID NO 199
<211> LENGTH: 33
<212> TYPE: DNA
<213> ORGANISM: Artificial Sequence
<220> FEATURE:
<223> OTHER INFORMATION: Synthetic

<400> SEQUENCE: 199
gctagagatc aaggagcagc agcactggac tac                             33

<210> SEQ ID NO 200
<211> LENGTH: 11
<212> TYPE: PRT
<213> ORGANISM: Artificial Sequence
<220> FEATURE:
<223> OTHER INFORMATION: Synthetic

<400> SEQUENCE: 200

Ala Arg Asp Gln Gly Ala Ala Ala Leu Asp Tyr
 1               5                   10

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccttccacc ctgtctgcat ctgtaggaga cagactcacc    60
atcacttgcc gggccagtca gagtatcaat aactggttgg cctggtatca gcagaaacca   120
gggaaagccc ctaaactcct gatctataag gcgtctaatt tagaaagtgg ggtcccatca   180
aggttcagcg gcagtggatc tgggacagaa ttcactctca ccatcagcaa tttgcagcct   240
gatgattttg caacttatta ctgccaacag tataatagtt ttttcctcac tttcggcgga   300
gggaccaagg tggagatcaa a                                    321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Thr Leu Ser Ala Ser Val Gly
1               5                   10                  15

Asp Arg Leu Thr Ile Thr Cys Arg Ala Ser Gln Ser Ile Asn Asn Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Asp Asp Phe Ala Thr Tyr Tyr Cys Gln Gln Tyr Asn Ser Phe Phe Leu
                85                  90                  95

Thr Phe Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatca ataactgg                                        18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Asn Asn Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggcgtct                                                  9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagtata atagtttttt cctcact                                            27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Ser Phe Phe Leu Thr
 1               5

<210> SEQ ID NO 209
<211> LENGTH: 357
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ctggtcaagc ctgggggtc cctgagactc          60 tcctgtgtag cctctggatt caccctcagt ggctatagca tgaactgggt ccgccaggct        120
ccagggaagg gcctggagtg gtctcatcc attagtacta gtagtagtta catatactac         180
gcagactcag tgcagggccg attcaccatc tccagagaca acgccaagaa ctcactgtat        240
ctgcaaatga acagcctgag agccgaggac acggctgtat attattgtgt gagaaagggc        300
gccaactgga tctactttga ctactggggc cagggaaccc tggtcaccgt ctcctca          357

<210> SEQ ID NO 210
<211> LENGTH: 119
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Lys Pro Gly Gly
 1               5                  10                  15

Ser Leu Arg Leu Ser Cys Val Ala Ser Gly Phe Thr Leu Ser Gly Tyr
             20                  25                  30

Ser Met Asn Trp Val Arg Gln Ala Pro Gly Lys Gly Leu Glu Trp Val
         35                  40                  45

Ser Ser Ile Ser Thr Ser Ser Ser Tyr Ile Tyr Ala Asp Ser Val
     50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Lys Gly Ala Asn Trp Ile Tyr Phe Asp Tyr Trp Gly Gln Gly
            100                 105                 110

Thr Leu Val Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcaccc tcagtggcta tagc                                          24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Leu Ser Gly Tyr Ser
 1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagtacta gtagtagtta cata                                          24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Thr Ser Ser Ser Tyr Ile
 1               5

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
gtgagaaagg gcgccaactg gatctacttt gactac                             36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Val Arg Lys Gly Ala Asn Trp Ile Tyr Phe Asp Tyr
1               5                   10

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217

```
gacatccaga tgacccagtc tccatcctcc gtgtctgctt ctgtaggaga cagagtcacc    60
atcacttgtc gggcgagtca gggtattagc agcttgttag cctggtttca gcagaaacca   120
gggaaagccc ctaacctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaaaagtt tcccattcac tttcggccct   300
gggaccaaag tggatatcaa a                                             321
```

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Leu
            20                  25                  30

Leu Ala Trp Phe Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Phe
                85                  90                  95

Thr Phe Gly Pro Gly Thr Lys Val Asp Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
cagggtatta gcagcttg                                                  18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Gly Ile Ser Ser Leu

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc					9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Ala Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacaggcta aaagtttccc attcact					27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Ala Lys Ser Phe Pro Phe Thr
 1               5

<210> SEQ ID NO 225
<211> LENGTH: 360
<212> TYPE: DNA
<213> ORGANISM: Artificial Sequence
<220> FEATURE:
<223> OTHER INFORMATION: Synthetic

<400> SEQUENCE: 225
caggtccagc tggtgcagtc tggggctgag gtgaagaagc ctgggtcctc ggtgaaggtc					60 tcctgcaagg cttctggagg caccttcagc agctatgcta tcagctgggt gcgacaggcc					120 cctggacaag ggcttgagtg gatgggaggg atcatcccct tctttggtac agcaacctac					180 gcacagaagt tccagggcag agtcacgatt accacggacg aatccacgag gacagtctac					240 atggaactga gcagcctgag atatgaggac acggccgtgt actactgtgc gagatggtat					300 agtggctacg ggggggactt tgactactgg ggccagggaa ccctggtcac cgtctcctca					360

<210> SEQ ID NO 226
<211> LENGTH: 120
<212> TYPE: PRT
<213> ORGANISM: Artificial Sequence
<220> FEATURE:
<223> OTHER INFORMATION: Synthetic

<400> SEQUENCE: 226

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Ala Thr Tyr Ala Gln Lys Phe
50                  55                  60

Gln Gly Arg Val Thr Ile Thr Thr Asp Glu Ser Thr Arg Thr Val Tyr
65                  70                  75                  80

Met Glu Leu Ser Ser Leu Arg Tyr Glu Asp Thr Ala Val Tyr Tyr Cys
                85                  90                  95

Ala Arg Trp Tyr Ser Gly Tyr Gly Gly Asp Phe Asp Tyr Trp Gly Gln
            100                 105                 110

Gly Thr Leu Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggaggcacct tcagcagcta tgct                                           24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Gly Thr Phe Ser Ser Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
atcatccctt tctttggtac agca                                           24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ile Pro Phe Phe Gly Thr Ala
1               5

<210> SEQ ID NO 231
<211> LENGTH: 39
<212> TYPE: DNA
<213> ORGANISM: Artificial Sequence
<220> FEATURE:
<223> OTHER INFORMATION: Synthetic

<400> SEQUENCE: 231
gcgagatggt atagtggcta cggggggggac tttgactac        39

<210> SEQ ID NO 232
<211> LENGTH: 13
<212> TYPE: PRT
<213> ORGANISM: Artificial Sequence
<220> FEATURE:
<223> OTHER INFORMATION: Synthetic

<400> SEQUENCE: 232

Ala Arg Trp Tyr Ser Gly Tyr Gly Gly Asp Phe Asp Tyr
1               5                   10

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233
gccatccaga tgacccagtc tccatcctcc ctgtctgcat ctgtaggaga cagagtcacc        60
atcacttgcc gggcaagtca gggcattaga aatgatttag gctggtttca gcagaaacca       120
gggaaagccc ctaagctcct gatctatgct gcatccagtt tacaaagtgg ggtcccatca       180
aggttcagcg gcagtggatc tggcacagat ttcactctct ccatcagcag cctgcagcct       240
gaagattttg caacttatta ctgtctacaa gattacagtt accctcggac gttcggccaa       300
gggaccaagg tggaaatcaa a                                                 321

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Leu Gln Asp Tyr Ser Tyr Pro Arg
                85                  90                  95

Thr Phe Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggcatta gaaatgat                                                    18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Arg Asn Asp
 1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcatcc                                                               9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
 1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
ctacaagatt acagttaccc tcggacg                                          27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Leu Gln Asp Tyr Ser Tyr Pro Arg Thr
 1               5

<210> SEQ ID NO 241
<211> LENGTH: 354
<212> TYPE: DNA
<213> ORGANISM: Artificial Sequence
<220> FEATURE:
<223> OTHER INFORMATION: Synthetic

<400> SEQUENCE: 241

```
caggtacaac tgctggagtc tgggggaggc gtggtccagc ctgggaagtc cctgagactc    60
tcctgtgtag cctctggatc catcttcagc atctatggca tgaactgggt ccgccaggct   120
ccaggcaagg gctggagtg gtggcaagt gtatcatctg atggcagtgc gaaattctat    180
gcagactccg tgaagggccg attcaccatc tccagagaca attccaatga cacgctcttt   240
ctgcaaatga ccagcctgag agctgaggac acggctgttt attactgtgc gaaaaccctt   300
tggaactacc tttttgactc atggggccag ggaaccctgg tcaccgtctc ctca         354
```

<210> SEQ ID NO 242
<211> LENGTH: 118
<212> TYPE: PRT
<213> ORGANISM: Artificial Sequence
<220> FEATURE:
<223> OTHER INFORMATION: Synthetic

<400> SEQUENCE: 242

Gln Val Gln Leu Leu Glu Ser Gly Gly Gly Val Val Gln Pro Gly Lys
1               5                   10                  15
Ser Leu Arg Leu Ser Cys Val Ala Ser Gly Ser Ile Phe Ser Ile Tyr
            20                  25                  30
Gly Met Asn Trp Val Arg Gln Ala Pro Gly Lys Gly Leu Glu Trp Val
        35                  40                  45
Ala Ser Val Ser Ser Asp Gly Ser Ala Lys Phe Tyr Ala Asp Ser Val
    50                  55                  60
Lys Gly Arg Phe Thr Ile Ser Arg Asp Asn Ser Asn Asp Thr Leu Phe
65                  70                  75                  80
Leu Gln Met Thr Ser Leu Arg Ala Glu Asp Thr Ala Val Tyr Tyr Cys
                85                  90                  95
Ala Lys Thr Leu Trp Asn Tyr Leu Phe Asp Ser Trp Gly Gln Gly Thr
            100                 105                 110
Leu Val Thr Val Ser Ser
        115

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggatccatct tcagcatcta tggc                                            24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Ser Ile Phe Ser Ile Tyr Gly
1               5

<210> SEQ ID NO 245
<211> LENGTH: 24

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
gtatcatctg atggcagtgc gaaa                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Val Ser Ser Asp Gly Ser Ala Lys
 1               5

<210> SEQ ID NO 247
<211> LENGTH: 33
<212> TYPE: DNA
<213> ORGANISM: Artificial Sequence
<220> FEATURE:
<223> OTHER INFORMATION: Synthetic

<400> SEQUENCE: 247
gcgaaaaccc tttggaacta ccttttttgac tca                               33

<210> SEQ ID NO 248
<211> LENGTH: 11
<212> TYPE: PRT
<213> ORGANISM: Artificial Sequence
<220> FEATURE:
<223> OTHER INFORMATION: Synthetic

<400> SEQUENCE: 248

Ala Lys Thr Leu Trp Asn Tyr Leu Phe Asp Ser
 1               5                  10

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gagaatgtgt tgacgcagtc tccagacacc ctgtctttgt ctccagggga gagagccacc     60
ctctcctgca gggccagtca gagtattacc agcaactatt tagcctggta ccagcagaaa    120
cctggccaga ctcccagact cctcatttct tttacatcca agggccac tggcatccca     180 gacaggttca gtggtagtgg gtctgggaca gtcttcactc tcaccatcag cagactggag    240
cctgaagatt ttgcagttta ttattgtcag cagtatggta cctcactcac tttcggcgga    300
ggggccaagg tggagatcag a                                             321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

-continued

Glu Asn Val Leu Thr Gln Ser Pro Asp Thr Leu Ser Leu Ser Pro Gly
1               5                   10                  15

Glu Arg Ala Thr Leu Ser Cys Arg Ala Ser Gln Ser Ile Thr Ser Asn
            20                  25                  30

Tyr Leu Ala Trp Tyr Gln Gln Lys Pro Gly Gln Thr Pro Arg Leu Leu
        35                  40                  45

Ile Ser Phe Thr Ser Arg Arg Ala Thr Gly Ile Pro Asp Arg Phe Ser
    50                  55                  60

Gly Ser Gly Ser Gly Thr Val Phe Thr Leu Thr Ile Ser Arg Leu Glu
65                  70                  75                  80

Pro Glu Asp Phe Ala Val Tyr Tyr Cys Gln Gln Tyr Gly Thr Ser Leu
                85                  90                  95

Thr Phe Gly Gly Gly Ala Lys Val Glu Ile Arg
            100                 105

<210> SEQ ID NO 251
<211> LENGTH: 21
<212> TYPE: DNA
<213> ORGANISM: Artificial Sequence
<220> FEATURE:
<223> OTHER INFORMATION: Synthetic

<400> SEQUENCE: 251
cagagtatta ccagcaacta t                                          21

<210> SEQ ID NO 252
<211> LENGTH: 7
<212> TYPE: PRT
<213> ORGANISM: Artificial Sequence
<220> FEATURE:
<223> OTHER INFORMATION: Synthetic

<400> SEQUENCE: 252

Gln Ser Ile Thr Ser Asn Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 tttacatcc                                                         9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Phe Thr Ser
1

<210> SEQ ID NO 255
<211> LENGTH: 24
<212> TYPE: DNA
<213> ORGANISM: Artificial Sequence
<220> FEATURE:
<223> OTHER INFORMATION: Synthetic -continued

<400> SEQUENCE: 255
cagcagtatg gtacctcact cact        24

<210> SEQ ID NO 256
<211> LENGTH: 8
<212> TYPE: PRT
<213> ORGANISM: Artificial Sequence
<220> FEATURE:
<223> OTHER INFORMATION: Synthetic

<400> SEQUENCE: 256

Gln Gln Tyr Gly Thr Ser Leu Thr
 1               5

<210> SEQ ID NO 257
<211> LENGTH: 360
<212> TYPE: DNA
<213> ORGANISM: Artificial Sequence
<220> FEATURE:
<223> OTHER INFORMATION: Synthetic

<400> SEQUENCE: 257
caggtccacc tggtgcagtc tggggctgag gtgaagaagc ctgggtcctc ggtgaaggtc        60
tcctgcaagg cttctggggg caccttcagc aactatgcta tcagctgggt gcgacaggcc       120
cctggtcaag gcttgagtg gatgggaggg atcatcccct tctctggttc agcgacctac       180
gcacagaatt ccagggcag aatcacgatt accacggacg aatccacgcg cacagcctac       240
atggaactga acggcctgag atctgaggac acggccgtgt attactgtgc gagatggttt       300
agtggctacg gggggactt tgactactgg ggccaggaa ccctggtcac cgtctcctca       360

<210> SEQ ID NO 258
<211> LENGTH: 120
<212> TYPE: PRT
<213> ORGANISM: Artificial Sequence
<220> FEATURE:
<223> OTHER INFORMATION: Synthetic

<400> SEQUENCE: 258

Gln Val His Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Ala Ile Ser Trp Val Arg Gln Ala Pro Gly Gln Gly Leu Glu Trp Met
            35                  40                  45

Gly Gly Ile Ile Pro Phe Ser Gly Ser Ala Thr Tyr Ala Gln Asn Phe
        50                  55                  60

Gln Gly Arg Ile Thr Ile Thr Thr Asp Glu Ser Thr Arg Thr Ala Tyr
 65                  70                  75                  80

Met Glu Leu Asn Gly Leu Arg Ser Glu Asp Thr Ala Val Tyr Tyr Cys
                85                  90                  95

Ala Arg Trp Phe Ser Gly Tyr Gly Gly Asp Phe Asp Tyr Trp Gly Gln
               100                 105                 110

Gly Thr Leu Val Thr Val Ser Ser
            115                 120

<210> SEQ ID NO 259
<211> LENGTH: 24
<212> TYPE: DNA
<213> ORGANISM: Artificial Sequence
<220> FEATURE:

<223> OTHER INFORMATION: Synthetic

<400> SEQUENCE: 259
gggggcacct tcagcaacta tgct                                              24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Gly Thr Phe Ser Asn Tyr Ala
 1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atcatccctt tctctggttc agcg                                              24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ile Pro Phe Ser Gly Ser Ala
 1               5

<210> SEQ ID NO 263
<211> LENGTH: 39
<212> TYPE: DNA
<213> ORGANISM: Artificial Sequence
<220> FEATURE:
<223> OTHER INFORMATION: Synthetic

<400> SEQUENCE: 263
gcgagatggt ttagtggcta cggggggggac tttgactac                             39

<210> SEQ ID NO 264
<211> LENGTH: 13
<212> TYPE: PRT
<213> ORGANISM: Artificial Sequence
<220> FEATURE:
<223> OTHER INFORMATION: Synthetic

<400> SEQUENCE: 264

Ala Arg Trp Phe Ser Gly Tyr Gly Gly Asp Phe Asp Tyr
 1               5                  10

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265

```
gccattcaga tgacccagtc tccatcctcc ctgtctgcat ctgttggaga cagagtcacc    60
atcacttgcc gggcaagtca ggacattaaa aatgatttag gctggtatca gcagaaacca   120
gggaaagccc ctaaactcct gatctatgct gcatccactt tacaaagtgg ggtcccatca   180
aggttcagcg gcagtggatc tggcacacat ttcactctca ccctcagcag cctgcagcct   240
gaagattttg caacttattt ctgtcttcag gattacactt tccctcggac gttcggccaa   300
gggaccaagg tggaaatcaa a                                             321
```

<210> SEQ ID NO 266
<211> LENGTH: 107
<212> TYPE: PRT
<213> ORGANISM: Artificial Sequence
<220> FEATURE:
<223> OTHER INFORMATION: Synthetic

<400> SEQUENCE: 266

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Lys Asn Asp
            20                  25                  30

Leu Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr His Phe Thr Leu Thr Leu Ser Ser Leu Gln Pro
65                  70                  75                  80

Glu Asp Phe Ala Thr Tyr Phe Cys Leu Gln Asp Tyr Thr Phe Pro Arg
                85                  90                  95

Thr Phe Gly Gln Gly Thr Lys Val Glu Ile Lys
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267

```
caggacatta aaaatgat                                                  18
```

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

```
Gln Asp Ile Lys Asn Asp
 1               5
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269

```
gctgcatcc                                                             9
```

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
 1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
cttcaggatt acactttccc tcggacg                                         27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Leu Gln Asp Tyr Thr Phe Pro Arg Thr
 1               5

<210> SEQ ID NO 273
<211> LENGTH: 360
<212> TYPE: DNA
<213> ORGANISM: Artificial Sequence
<220> FEATURE:
<223> OTHER INFORMATION: Synthetic

<400> SEQUENCE: 273
caggtccaac tggtgcagtc tggggctgag gtgaagaagc ctgggtcctc ggttaaggtc      60
tcctgcaagg cttctggagg caccttcacc aactttgcta tcagctgggt gcgacaggcc    120
cctggactgg gcttgaatg gatgggaggg atcatccctt tcgttgggac agcaacctac    180
gaacagaagt tccagggcag agtctcgatt accgcggacg agtccacgag gaccgcttac    240
atggaactga gcagtctgag atatgatgac acggccgtgt actactgtgc gagatggttt    300
agtggctccg gggggactt tgactactgg ggccagggaa ccctggtcac cgtctcctca    360

<210> SEQ ID NO 274
<211> LENGTH: 120
<212> TYPE: PRT
<213> ORGANISM: Artificial Sequence
<220> FEATURE:
<223> OTHER INFORMATION: Synthetic

<400> SEQUENCE: 274

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Thr Asn Phe
            20                  25                  30

Ala Ile Ser Trp Val Arg Gln Ala Pro Gly Leu Gly Leu Glu Trp Met
        35                  40                  45

Gly Gly Ile Ile Pro Phe Val Gly Thr Ala Thr Tyr Glu Gln Lys Phe
        50                  55                  60

Gln Gly Arg Val Ser Ile Thr Ala Asp Glu Ser Thr Arg Thr Ala Tyr
 65                  70                  75                  80

Met Glu Leu Ser Ser Leu Arg Tyr Asp Asp Thr Ala Val Tyr Tyr Cys
                85                  90                  95

Ala Arg Trp Phe Ser Gly Ser Gly Gly Asp Phe Asp Tyr Trp Gly Gln
            100                 105                 110

Gly Thr Leu Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggaggcacct tcaccaactt tgct                                      24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Gly Thr Phe Thr Asn Phe Ala
  1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
atcatccctt tcgttgggac agca                                      24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ile Pro Phe Val Gly Thr Ala
  1               5

<210> SEQ ID NO 279
<211> LENGTH: 39
<212> TYPE: DNA
<213> ORGANISM: Artificial Sequence
<220> FEATURE:
<223> OTHER INFORMATION: Synthetic

<400> SEQUENCE: 279
gcgagatggt ttagtggctc cggggggac tttgactac                       39

-continued

<210> SEQ ID NO 280
<211> LENGTH: 13
<212> TYPE: PRT
<213> ORGANISM: Artificial Sequence
<220> FEATURE:
<223> OTHER INFORMATION: Synthetic

<400> SEQUENCE: 280

Ala Arg Trp Phe Ser Gly Ser Gly Gly Asp Phe Asp Tyr
1               5                   10

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281
gccatccaga tgacccagtc tccatcctcc ctgtctgcat ctgtaggaga cagagtcacc      60
atcacttgcc gggcaagtca gggcattgga aatgatttag gctggtatca acagagacga     120
gggacagccc ctaagctcct gatctatgct gcatccagtt tacaaagtgg ggtcccatca     180
aggttcagcg gcagtggatc tggcacagat ttcactctca ccatcagcag cctacagcct     240
gaagattttg caacttatta ctgtctacaa gatttcactt tccctcggac gttcggccaa     300
gggaccaagg tggaaatcaa a                                                321

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
                20                  25                  30

Leu Gly Trp Tyr Gln Gln Arg Arg Gly Thr Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Thr Phe Pro Arg
                85                  90                  95

Thr Phe Gly Gln Gly Thr Lys Val Glu Ile Lys
            100                 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagggcattg gaaatgat                                                     18

<210> SEQ ID NO 284

```
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Gly Ile Gly Asn Asp
  1               5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gctgcatcc                                                                 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
  1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
ctacaagatt tcactttccc tcggacg                                            27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Leu Gln Asp Phe Thr Phe Pro Arg Thr
  1               5

<210> SEQ ID NO 289
<211> LENGTH: 410
<212> TYPE: PRT
<213> ORGANISM: Trypanosoma brucei

<400> SEQUENCE: 289

Met Pro Arg Asn Ser Gly Arg Thr Thr Ser Thr Leu Ala Leu Ala Val
  1               5                  10                  15

Ala Leu Lys Leu Leu Ala Val Pro Val Ser Pro Ser Gly Thr Ala Phe
                 20                  25                  30

Asp Glu Glu Pro Val Lys Lys Val Cys Lys Val Glu Lys Asn Leu Ala
         35                  40                  45

Asp Val Ala Gly Ile Ala Leu Ala Lys Ile Asn Asn Leu Ile Lys Gln
```

```
              50                  55                  60
Val Ser Ala Ala Thr Glu Ala Glu Ala Arg Met Thr Leu Ala Ala Ala
 65                  70                  75                  80

Ser Thr Asp His Ser Asn Ile Ser Ala Leu Tyr Ala Ala Ser Asn
                 85                  90                  95

Ile Val Thr Arg Cys Val Leu Asn Ala Val His Ala Leu Thr Ser Leu
                100                 105                 110

Ala Pro Ile Ala Leu Thr Ala Ala Thr Asn Gly Ala Lys Thr Ser Gly
                115                 120                 125

His Ile Ser Glu Val Ile Asp Ile Leu Gln Gln Ala Ser Gln Gly Lys
            130                 135                 140

Thr Glu Gly Lys Cys Ile Val Lys Ser Gly Gly Thr Thr Thr Val
145                 150                 155                 160

Ala Ile Arg Gln Leu Tyr Asn Lys Ile Gly Asp Leu Glu Lys Gln Thr
                165                 170                 175

Thr Asn Asn Cys Gly Thr Ser Val Thr Glu Val Leu Glu His Ile Leu
                180                 185                 190

Lys Gln Glu Ala Leu Lys Glu Ala Val Leu Ser Ile Val Lys Lys Pro
            195                 200                 205

Lys Gly Ala Pro Asp Lys Thr Ala Ala Asp Glu Leu Val Thr Ala Leu
210                 215                 220

Ile Asn Gly Val Val Pro Asn Ser Thr Ala Gln Thr Gln Lys Leu Lys
225                 230                 235                 240

Glu Lys Ile Leu Asn Thr Leu Val Pro Lys Leu Val Glu Gly Ser Lys
                245                 250                 255

Ser Gln Val Lys Leu Arg Ile Leu Lys Tyr Pro Gly Lys Ile Gln Lys
                260                 265                 270

Ser Lys Leu Val Ser Ile Gln Glu Leu Lys Thr Arg Val Glu Pro Glu
            275                 280                 285

Ser Ser Thr Glu Ser Cys Lys Gln Gln Val Ala Thr Asn Gln Ala Gln
290                 295                 300

Glu Ala Phe Cys Asn Ala Ile Gly Asp Asp Lys Asp Lys Cys Asn Asn
305                 310                 315                 320

Glu Thr Arg Cys Ser Tyr Asp Asp Ser Lys Gly Ser Asp Lys Lys Cys
                325                 330                 335

Thr Tyr Asn Ala Glu Lys Ala Glu Ala Asn Gly Ala Pro Ala Thr Gln
                340                 345                 350

Pro Gln Gly Gly Val Asn Glu Ala Thr Thr Gly Asn Cys Lys Gly Lys
            355                 360                 365

Leu Glu Pro Gly Cys Thr Lys Ala Gln Glu Tyr Glu Trp Glu Gly Lys
370                 375                 380

Glu Ser Lys Asp Ser Ser Phe Leu Val Asp Met Lys Leu Ala Leu Asn
385                 390                 395                 400

Met Val Ala Ala Phe Val Ala Phe Leu Phe
                405                 410

<210> SEQ ID NO 290
<211> LENGTH: 245
<212> TYPE: PRT
<213> ORGANISM: Artificial Sequence
<220> FEATURE:
<223> OTHER INFORMATION: Synthetic

<400> SEQUENCE: 290

Gly Ala Phe Asp Glu Glu Pro Val Lys Lys Val Cys Lys Val Glu Lys
```

```
                 1               5                  10                  15
              Asn Leu Ala Asp Val Ala Gly Ile Ala Leu Ala Lys Ile Asn Asn Leu
                              20                  25                  30
              Ile Lys Gln Val Ser Ala Ala Thr Glu Ala Glu Ala Arg Met Thr Leu
                              35                  40                  45
              Ala Ala Ala Ser Thr Asp His Ser Asn Ile Ser Ala Leu Tyr Ala Ala
               50                  55                  60
              Ala Ser Asn Ile Val Thr Arg Cys Val Leu Asn Ala Val His Ala Leu
               65                  70                  75                  80
              Thr Ser Leu Ala Pro Ile Ala Leu Thr Ala Ala Thr Asn Gly Ala Lys
                              85                  90                  95
              Thr Ser Gly His Ile Ser Glu Val Ile Asp Ile Leu Gln Gln Ala Ser
                             100                 105                 110
              Gln Gly Lys Thr Glu Gly Lys Cys Ile Val Lys Ser Gly Gly Thr
                             115                 120                 125
              Thr Thr Val Ala Ile Arg Gln Leu Tyr Asn Lys Ile Gly Asp Leu Glu
                             130                 135                 140
              Lys Gln Thr Thr Asn Asn Cys Gly Thr Ser Val Thr Glu Val Leu Glu
              145                 150                 155                 160
              His Ile Leu Lys Gln Glu Ala Leu Lys Glu Ala Leu Leu Ser Ile Val
                             165                 170                 175
              Lys Lys Pro Lys Gly Ala Pro Asp Lys Thr Ala Ala Asp Glu Leu Val
                             180                 185                 190
              Thr Ala Leu Ile Asn Gly Val Val Pro Asn Ser Thr Ala Gln Thr Gln
                             195                 200                 205
              Lys Leu Lys Glu Lys Ile Leu Asn Thr Leu Val Pro Lys Leu Val Glu
                             210                 215                 220
              Gly Ser Lys Ser Gln Val Lys Leu Arg Ile Leu Lys Tyr Pro Gly Lys
              225                 230                 235                 240
              Ile Gln Lys Ser Lys
                             245

<210> SEQ ID NO 291
<211> LENGTH: 303
<212> TYPE: PRT
<213> ORGANISM: Artificial Sequence
<220> FEATURE:
<223> OTHER INFORMATION: Synthetic

<400> SEQUENCE: 291

Met His Arg Pro Arg Arg Gly Thr Arg Pro Pro Leu Ala Leu
              1                  5                  10                  15
              Leu Ala Leu Leu Leu Ala Ala Arg Gly Ala Asp Ala Gly Thr Ala
                              20                  25                  30
              Phe Asp Glu Glu Pro Val Lys Lys Val Cys Lys Val Glu Lys Asn Leu
                              35                  40                  45
              Ala Asp Val Ala Gly Ile Ala Leu Ala Lys Ile Asn Asn Leu Ile Lys
               50                  55                  60
              Gln Val Ser Ala Ala Thr Glu Ala Glu Ala Arg Met Thr Leu Ala Ala
               65                  70                  75                  80
              Ala Ser Thr Asp His Ser Asn Ile Ser Ala Leu Tyr Ala Ala Ala Ser
                              85                  90                  95
              Asn Ile Val Thr Arg Cys Val Leu Asn Ala Val His Ala Leu Thr Ser
                             100                 105                 110
              Leu Ala Pro Ile Ala Leu Thr Ala Ala Thr Asn Gly Ala Lys Thr Ser
```

```
                115                 120                 125
Gly His Ile Ser Glu Val Ile Asp Ile Leu Gln Gln Ala Ser Gln Gly
        130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
            180                 185                 190

Leu Lys Gln Glu Ala Leu Lys Glu Ala Leu Leu Ser Ile Val Lys Lys
        195                 200                 205

Pro Lys Gly Ala Pro Asp Lys Thr Ala Ala Asp Glu Leu Val Thr Ala
210                 215                 220

Leu Ile Asn Gly Val Val Pro Asn Ser Thr Ala Gln Thr Gln Lys Leu
225                 230                 235                 240

Lys Glu Lys Ile Leu Asn Thr Leu Val Pro Lys Leu Val Glu Gly Ser
                245                 250                 255

Lys Ser Gln Val Lys Leu Arg Ile Leu Lys Tyr Pro Gly Lys Ile Gln
            260                 265                 270

Lys Ser Lys Glu Gln Lys Leu Ile Ser Glu Glu Asp Leu Gly Gly Glu
        275                 280                 285

Gln Lys Leu Ile Ser Glu Glu Asp Leu His His His His His His
290                 295                 300
```

<210> SEQ ID NO 292
<211> LENGTH: 508
<212> TYPE: PRT
<213> ORGANISM: Artificial Sequence
<220> FEATURE:
<223> OTHER INFORMATION: Synthetic

<400> SEQUENCE: 292

```
Met His Arg Pro Arg Arg Gly Thr Arg Pro Pro Leu Ala Leu
1               5                   10                  15

Leu Ala Leu Leu Leu Ala Ala Arg Gly Ala Asp Ala Gly Thr Ala
            20                  25                  30

Phe Asp Glu Glu Pro Val Lys Lys Val Cys Lys Val Glu Lys Asn Leu
            35                  40                  45

Ala Asp Val Ala Gly Ile Ala Leu Ala Lys Ile Asn Asn Leu Ile Lys
        50                  55                  60

Gln Val Ser Ala Ala Thr Glu Ala Glu Ala Arg Met Thr Leu Ala Ala
65                  70                  75                  80

Ala Ser Thr Asp His Ser Asn Ile Ser Ala Leu Tyr Ala Ala Ala Ser
                85                  90                  95

Asn Ile Val Thr Arg Cys Val Leu Asn Ala Val His Ala Leu Thr Ser
            100                 105                 110

Leu Ala Pro Ile Ala Leu Thr Ala Ala Thr Asn Gly Ala Lys Thr Ser
        115                 120                 125

Gly His Ile Ser Glu Val Ile Asp Ile Leu Gln Gln Ala Ser Gln Gly
    130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
```

```
                180             185             190
Leu Lys Gln Glu Ala Leu Lys Glu Ala Leu Leu Ser Ile Val Lys Lys
            195                 200                 205
Pro Lys Gly Ala Pro Asp Lys Thr Ala Asp Glu Leu Val Thr Ala
        210                 215                 220
Leu Ile Asn Gly Val Val Pro Asn Ser Thr Ala Gln Thr Gln Lys Leu
225                 230                 235                 240
Lys Glu Lys Ile Leu Asn Thr Leu Val Pro Lys Leu Val Glu Gly Ser
                245                 250                 255
Lys Ser Gln Val Lys Leu Arg Ile Leu Lys Tyr Pro Gly Lys Ile Gln
            260                 265                 270
Lys Ser Lys Glu Pro Arg Gly Pro Thr Ile Lys Pro Cys Pro Pro Cys
        275                 280                 285
Lys Cys Pro Ala Pro Asn Leu Leu Gly Gly Pro Ser Val Phe Ile Phe
        290                 295                 300
Pro Pro Lys Ile Lys Asp Val Leu Met Ile Ser Leu Ser Pro Ile Val
305                 310                 315                 320
Thr Cys Val Val Val Asp Val Ser Glu Asp Asp Pro Asp Val Gln Ile
                325                 330                 335
Ser Trp Phe Val Asn Asn Val Glu Val His Thr Ala Gln Thr Gln Thr
                340                 345                 350
His Arg Glu Asp Tyr Asn Ser Thr Leu Arg Val Val Ser Ala Leu Pro
            355                 360                 365
Ile Gln His Gln Asp Trp Met Ser Gly Lys Glu Phe Lys Cys Lys Val
        370                 375                 380
Asn Asn Lys Asp Leu Pro Ala Pro Ile Glu Arg Thr Ile Ser Lys Pro
385                 390                 395                 400
Lys Gly Ser Val Arg Ala Pro Gln Val Tyr Val Leu Pro Pro Pro Glu
                405                 410                 415
Glu Glu Met Thr Lys Lys Gln Val Thr Leu Thr Cys Met Val Thr Asp
            420                 425                 430
Phe Met Pro Glu Asp Ile Tyr Val Glu Trp Thr Asn Asn Gly Lys Thr
        435                 440                 445
Glu Leu Asn Tyr Lys Asn Thr Glu Pro Val Leu Asp Ser Asp Gly Ser
    450                 455                 460
Tyr Phe Met Tyr Ser Lys Leu Arg Val Glu Lys Lys Asn Trp Val Glu
465                 470                 475                 480
Arg Asn Ser Tyr Ser Cys Ser Val Val His Glu Gly Leu His Asn His
                485                 490                 495
His Thr Thr Lys Ser Phe Ser Arg Thr Pro Gly Lys
                500                 505

<210> SEQ ID NO 293
<211> LENGTH: 502
<212> TYPE: PRT
<213> ORGANISM: Artificial Sequence
<220> FEATURE:
<223> OTHER INFORMATION: Synthetic

<400> SEQUENCE: 293

Met His Arg Pro Arg Arg Gly Thr Arg Pro Pro Leu Ala Leu
1               5                   10                  15

Leu Ala Leu Leu Leu Ala Ala Arg Gly Ala Asp Ala Gly Thr Ala
            20                  25                  30

Phe Asp Glu Glu Pro Val Lys Lys Val Cys Lys Val Glu Lys Asn Leu
```

```
                35                  40                  45
Ala Asp Val Ala Gly Ile Ala Leu Ala Lys Ile Asn Asn Leu Ile Lys
 50                  55                  60

Gln Val Ser Ala Ala Thr Glu Ala Glu Ala Arg Met Thr Leu Ala Ala
 65                  70                  75                  80

Ala Ser Thr Asp His Ser Asn Ile Ser Ala Leu Tyr Ala Ala Ala Ser
                 85                  90                  95

Asn Ile Val Thr Arg Cys Val Leu Asn Ala Val His Ala Leu Thr Ser
                100                 105                 110

Leu Ala Pro Ile Ala Leu Thr Ala Ala Thr Asn Gly Ala Lys Thr Ser
                115                 120                 125

Gly His Ile Ser Glu Val Ile Asp Ile Leu Gln Gln Ala Ser Gln Gly
                130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
                180                 185                 190

Leu Lys Gln Glu Ala Leu Lys Glu Ala Leu Leu Ser Ile Val Lys Lys
                195                 200                 205

Pro Lys Gly Ala Pro Asp Lys Thr Ala Ala Asp Glu Leu Val Thr Ala
210                 215                 220

Leu Ile Asn Gly Val Val Pro Asn Ser Thr Ala Gln Thr Gln Lys Leu
225                 230                 235                 240

Lys Glu Lys Ile Leu Asn Thr Leu Val Pro Lys Leu Val Glu Gly Ser
                245                 250                 255

Lys Ser Gln Val Lys Leu Arg Ile Leu Lys Tyr Pro Gly Lys Ile Gln
                260                 265                 270

Lys Ser Lys Asp Lys Thr His Thr Cys Pro Pro Cys Pro Ala Pro Glu
                275                 280                 285

Leu Leu Gly Gly Pro Ser Val Phe Leu Phe Pro Pro Lys Pro Lys Asp
                290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
                340                 345                 350

Ser Thr Tyr Arg Val Val Ser Val Leu Thr Val Leu His Gln Asp Trp
                355                 360                 365

Leu Asn Gly Lys Glu Tyr Lys Cys Lys Val Ser Asn Lys Ala Leu Pro
                370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
                435                 440                 445

Thr Pro Pro Val Leu Asp Ser Asp Gly Ser Phe Phe Leu Tyr Ser Lys
450                 455                 460
```

-continued

```
Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 294
<211> LENGTH: 417
<212> TYPE: PRT
<213> ORGANISM: Artificial Sequence
<220> FEATURE:
<223> OTHER INFORMATION: Synthetic

<400> SEQUENCE: 294

Met His Arg Pro Arg Arg Gly Thr Arg Pro Pro Leu Ala Leu
  1               5                  10                  15

Leu Ala Ala Leu Leu Leu Ala Ala Arg Gly Ala Asp Ala Gly Thr Ala
                20                  25                  30

Phe Asp Glu Glu Pro Val Lys Lys Val Cys Lys Val Glu Lys Asn Leu
            35                  40                  45

Ala Asp Val Ala Gly Ile Ala Leu Ala Lys Ile Asn Asn Leu Ile Lys
        50                  55                  60

Gln Val Ser Ala Ala Thr Glu Ala Glu Ala Arg Met Thr Leu Ala Ala
 65                 70                  75                  80

Ala Ser Thr Asp His Ser Asn Ile Ser Ala Leu Tyr Ala Ala Ala Ser
                85                  90                  95

Asn Ile Val Thr Arg Cys Val Leu Asn Ala Val His Ala Leu Thr Ser
            100                 105                 110

Leu Ala Pro Ile Ala Leu Thr Ala Ala Thr Asn Gly Ala Lys Thr Ser
        115                 120                 125

Gly His Ile Ser Glu Val Ile Asp Ile Leu Gln Gln Ala Ser Gln Gly
    130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
            180                 185                 190

Leu Lys Gln Glu Ala Leu Lys Glu Ala Leu Leu Ser Ile Val Lys Lys
        195                 200                 205

Pro Lys Gly Ala Pro Asp Lys Thr Ala Ala Asp Glu Leu Val Thr Ala
    210                 215                 220

Leu Ile Asn Gly Val Val Pro Asn Ser Thr Ala Gln Thr Gln Lys Leu
225                 230                 235                 240

Lys Glu Lys Ile Leu Asn Thr Leu Val Pro Lys Leu Val Glu Gly Ser
                245                 250                 255

Lys Ser Gln Val Lys Leu Arg Ile Leu Lys Tyr Pro Gly Lys Ile Gln
            260                 265                 270

Lys Ser Lys Leu Val Ser Ile Gln Glu Leu Lys Thr Arg Val Glu Pro
        275                 280                 285

Glu Ser Ser Thr Glu Ser Cys Lys Gln Gln Val Ala Thr Asn Gln Ala
    290                 295                 300

Gln Glu Ala Phe Cys Asn Ala Ile Gly Asp Asp Lys Asp Lys Cys Asn
305                 310                 315                 320
```

```
Asn Glu Thr Arg Cys Ser Tyr Asp Asp Ser Lys Gly Ser Asp Lys Lys
                325                 330                 335

Cys Thr Tyr Asn Ala Glu Lys Ala Glu Ala Asn Gly Ala Pro Ala Thr
            340                 345                 350

Gln Pro Gln Gly Gly Val Asn Glu Ala Thr Thr Gly Asn Cys Lys Gly
        355                 360                 365

Lys Leu Glu Pro Gly Cys Thr Lys Ala Gln Glu Tyr Glu Trp Glu Gly
    370                 375                 380

Lys Glu Ser Lys Asp Glu Gln Lys Leu Ile Ser Glu Glu Asp Leu Gly
385                 390                 395                 400

Gly Glu Gln Lys Leu Ile Ser Glu Glu Asp Leu His His His His His
                405                 410                 415

His

<210> SEQ ID NO 295
<211> LENGTH: 622
<212> TYPE: PRT
<213> ORGANISM: Artificial Sequence
<220> FEATURE:
<223> OTHER INFORMATION: Synthetic

<400> SEQUENCE: 295

Met His Arg Pro Arg Arg Gly Thr Arg Pro Pro Leu Ala Leu
1               5                   10                  15

Leu Ala Ala Leu Leu Ala Ala Arg Gly Ala Asp Ala Gly Thr Ala
                20                  25                  30

Phe Asp Glu Glu Pro Val Lys Lys Val Cys Lys Val Glu Lys Asn Leu
            35                  40                  45

Ala Asp Val Ala Gly Ile Ala Leu Ala Lys Ile Asn Asn Leu Ile Lys
50                  55                  60

Gln Val Ser Ala Ala Thr Glu Ala Glu Ala Arg Met Thr Leu Ala Ala
65                  70                  75                  80

Ala Ser Thr Asp His Ser Asn Ile Ser Ala Leu Tyr Ala Ala Ala Ser
                85                  90                  95

Asn Ile Val Thr Arg Cys Val Leu Asn Ala Val His Ala Leu Thr Ser
                100                 105                 110

Leu Ala Pro Ile Ala Leu Thr Ala Ala Thr Asn Gly Ala Lys Thr Ser
            115                 120                 125

Gly His Ile Ser Glu Val Ile Asp Ile Leu Gln Gln Ala Ser Gln Gly
    130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
                180                 185                 190

Leu Lys Gln Glu Ala Leu Lys Glu Ala Leu Leu Ser Ile Val Lys Lys
            195                 200                 205

Pro Lys Gly Ala Pro Asp Lys Thr Ala Ala Asp Glu Leu Val Thr Ala
    210                 215                 220

Leu Ile Asn Gly Val Val Pro Asn Ser Thr Ala Gln Thr Gln Lys Leu
225                 230                 235                 240

Lys Glu Lys Ile Leu Asn Thr Leu Val Pro Lys Leu Val Glu Gly Ser
                245                 250                 255
```

Lys Ser Gln Val Lys Leu Arg Ile Leu Lys Tyr Pro Gly Lys Ile Gln
        260                 265                 270

Lys Ser Lys Leu Val Ser Ile Gln Glu Leu Lys Thr Arg Val Glu Pro
    275                 280                 285

Glu Ser Ser Thr Glu Ser Cys Lys Gln Val Ala Thr Asn Gln Ala
290                 295                 300

Gln Glu Ala Phe Cys Asn Ala Ile Gly Asp Lys Asp Lys Cys Asn
305                 310                 315                 320

Asn Glu Thr Arg Cys Ser Tyr Asp Asp Ser Lys Gly Ser Asp Lys Lys
            325                 330                 335

Cys Thr Tyr Asn Ala Glu Lys Ala Glu Ala Asn Gly Ala Pro Ala Thr
        340                 345                 350

Gln Pro Gln Gly Gly Val Asn Glu Ala Thr Thr Gly Asn Cys Lys Gly
        355                 360                 365

Lys Leu Glu Pro Gly Cys Thr Lys Ala Gln Glu Tyr Glu Trp Glu Gly
    370                 375                 380

Lys Glu Ser Lys Asp Glu Pro Arg Gly Pro Thr Ile Lys Pro Cys Pro
385                 390                 395                 400

Pro Cys Lys Cys Pro Ala Pro Asn Leu Leu Gly Gly Pro Ser Val Phe
            405                 410                 415

Ile Phe Pro Pro Lys Ile Lys Asp Val Leu Met Ile Ser Leu Ser Pro
        420                 425                 430

Ile Val Thr Cys Val Val Val Asp Val Ser Glu Asp Asp Pro Asp Val
    435                 440                 445

Gln Ile Ser Trp Phe Val Asn Asn Val Glu Val His Thr Ala Gln Thr
450                 455                 460

Gln Thr His Arg Glu Asp Tyr Asn Ser Thr Leu Arg Val Val Ser Ala
465                 470                 475                 480

Leu Pro Ile Gln His Gln Asp Trp Met Ser Gly Lys Glu Phe Lys Cys
            485                 490                 495

Lys Val Asn Asn Lys Asp Leu Pro Ala Pro Ile Glu Arg Thr Ile Ser
        500                 505                 510

Lys Pro Lys Gly Ser Val Arg Ala Pro Gln Val Tyr Val Leu Pro Pro
    515                 520                 525

Pro Glu Glu Glu Met Thr Lys Lys Gln Val Thr Leu Thr Cys Met Val
530                 535                 540

Thr Asp Phe Met Pro Glu Asp Ile Tyr Val Glu Trp Thr Asn Asn Gly
545                 550                 555                 560

Lys Thr Glu Leu Asn Tyr Lys Asn Thr Glu Pro Val Leu Asp Ser Asp
            565                 570                 575

Gly Ser Tyr Phe Met Tyr Ser Lys Leu Arg Val Glu Lys Lys Asn Trp
        580                 585                 590

Val Glu Arg Asn Ser Tyr Ser Cys Ser Val Val His Glu Gly Leu His
    595                 600                 605

Asn His His Thr Thr Lys Ser Phe Ser Arg Thr Pro Gly Lys
        610                 615                 620

<210> SEQ ID NO 296
<211> LENGTH: 616
<212> TYPE: PRT
<213> ORGANISM: Artificial Sequence
<220> FEATURE:
<223> OTHER INFORMATION: Synthetic

<400> SEQUENCE: 296

-continued

```
Met His Arg Pro Arg Arg Gly Thr Arg Pro Pro Leu Ala Leu
 1               5                  10              15

Leu Ala Ala Leu Leu Ala Ala Arg Gly Ala Asp Ala Gly Thr Ala
            20                  25              30

Phe Asp Glu Glu Pro Val Lys Lys Val Cys Lys Val Glu Lys Asn Leu
            35                  40                  45

Ala Asp Val Ala Gly Ile Ala Leu Ala Lys Ile Asn Asn Leu Ile Lys
     50                  55                  60

Gln Val Ser Ala Ala Thr Glu Ala Glu Ala Arg Met Thr Leu Ala Ala
 65                  70                  75                  80

Ala Ser Thr Asp His Ser Asn Ile Ser Ala Leu Tyr Ala Ala Ser
                85                  90                  95

Asn Ile Val Thr Arg Cys Val Leu Asn Ala Val His Ala Leu Thr Ser
                100                 105                 110

Leu Ala Pro Ile Ala Leu Thr Ala Ala Thr Asn Gly Ala Lys Thr Ser
            115                 120                 125

Gly His Ile Ser Glu Val Ile Asp Ile Leu Gln Gln Ala Ser Gln Gly
        130                 135                 140

Lys Thr Glu Gly Lys Cys Ile Val Lys Ser Gly Gly Thr Thr Thr
145                 150                 155                 160

Val Ala Ile Arg Gln Leu Tyr Asn Lys Ile Gly Asp Leu Glu Lys Gln
                165                 170                 175

Thr Thr Asn Asn Cys Gly Thr Ser Val Thr Glu Val Leu Glu His Ile
                180                 185                 190

Leu Lys Gln Glu Ala Leu Lys Glu Ala Leu Leu Ser Ile Val Lys Lys
            195                 200                 205

Pro Lys Gly Ala Pro Asp Lys Thr Ala Ala Asp Glu Leu Val Thr Ala
210                 215                 220

Leu Ile Asn Gly Val Val Pro Asn Ser Thr Ala Gln Thr Gln Lys Leu
225                 230                 235                 240

Lys Glu Lys Ile Leu Asn Thr Leu Val Pro Lys Leu Val Glu Gly Ser
                245                 250                 255

Lys Ser Gln Val Lys Leu Arg Ile Leu Lys Tyr Pro Gly Lys Ile Gln
            260                 265                 270

Lys Ser Lys Leu Val Ser Ile Gln Glu Leu Lys Thr Arg Val Glu Pro
        275                 280                 285

Glu Ser Ser Thr Glu Ser Cys Lys Gln Gln Val Ala Thr Asn Gln Ala
        290                 295                 300

Gln Glu Ala Phe Cys Asn Ala Ile Gly Asp Asp Lys Asp Lys Cys Asn
305                 310                 315                 320

Asn Glu Thr Arg Cys Ser Tyr Asp Asp Ser Lys Gly Ser Asp Lys Lys
                325                 330                 335

Cys Thr Tyr Asn Ala Glu Lys Ala Glu Ala Asn Gly Ala Pro Ala Thr
            340                 345                 350

Gln Pro Gln Gly Gly Val Asn Glu Ala Thr Thr Gly Asn Cys Lys Gly
        355                 360                 365

Lys Leu Glu Pro Gly Cys Thr Lys Ala Gln Glu Tyr Glu Trp Glu Gly
    370                 375                 380

Lys Glu Ser Lys Asp Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
```

```
                420                 425                 430
Val Asp Val Ser His Glu Asp Pro Glu Val Lys Phe Asn Trp Tyr Val
                435                 440                 445

Asp Gly Val Glu Val His Asn Ala Lys Thr Lys Pro Arg Glu Glu Gln
        450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
            500                 505                 510

Arg Glu Pro Gln Val Tyr Thr Leu Pro Pro Ser Arg Asp Glu Leu Thr
            515                 520                 525

Lys Asn Gln Val Ser Leu Thr Cys Leu Val Lys Gly Phe Tyr Pro Ser
        530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys
    610                 615

<210> SEQ ID NO 297
<211> LENGTH: 46
<212> TYPE: PRT
<213> ORGANISM: Artificial Sequence
<220> FEATURE:
<223> OTHER INFORMATION: Synthetic

<400> SEQUENCE: 297

Val Tyr Glu Ser Lys His Leu His Glu Gly Ala Lys Ser Glu Thr Ala
1               5                   10                  15

Glu Glu Leu Lys Lys Val Ala Gln Glu Leu Glu Glu Lys Leu Asn Ile
                20                  25                  30

Leu Asn Asn Asn Tyr Lys Ile Leu Gln Ala Asp Gln Glu Leu
            35                  40                  45

<210> SEQ ID NO 298
<211> LENGTH: 34
<212> TYPE: PRT
<213> ORGANISM: Artificial Sequence
<220> FEATURE:
<223> OTHER INFORMATION: Synthetic

<400> SEQUENCE: 298

Ser Glu Thr Ala Glu Glu Leu Lys Lys Val Ala Gln Glu Leu Glu Glu
1               5                   10                  15

Lys Leu Asn Ile Leu Asn Asn Asn Tyr Lys Ile Leu Gln Ala Asp Gln
                20                  25                  30

Glu Leu

<210> SEQ ID NO 299
<211> LENGTH: 44
<212> TYPE: PRT
```

```
<213> ORGANISM: Artificial Sequence
<220> FEATURE:
<223> OTHER INFORMATION: Synthetic

<400> SEQUENCE: 299

Val Cys Gln Leu Lys His Leu His Glu Gly Ala Lys Ser Lys Thr Ala
1               5                   10                  15

Glu Glu Leu Lys Lys Val Ala Gln Glu Leu Glu Lys Lys Leu Asn Ile
            20                  25                  30

Leu Asn Lys Lys Tyr Glu Thr Leu Arg Gln Glu Pro
        35                  40

<210> SEQ ID NO 300
<211> LENGTH: 34
<212> TYPE: PRT
<213> ORGANISM: Artificial Sequence
<220> FEATURE:
<223> OTHER INFORMATION: Synthetic

<400> SEQUENCE: 300

Ser Glu Thr Ala Glu Glu Leu Lys Lys Val Ala Gln Glu Leu Glu Glu
1               5                   10                  15

Lys Leu Asn Ile Leu Asn Lys Lys Tyr Lys Ile Leu Gln Ala Asp Gln
            20                  25                  30

Glu Leu

<210> SEQ ID NO 301
<211> LENGTH: 21
<212> TYPE: PRT
<213> ORGANISM: Artificial Sequence
<220> FEATURE:
<223> OTHER INFORMATION: Synthetic

<400> SEQUENCE: 301

Leu Ser Ile Val Lys Lys Pro Lys Gly Ala Pro Asp Lys Thr Ala Ala
1               5                   10                  15

Asp Glu Leu Val Thr
            20
```